(12) United States Patent
Farascioni et al.

(10) Patent No.: US 9,474,578 B2
(45) Date of Patent: *Oct. 25, 2016

(54) LOCKING SHIPPING WEDGE

(71) Applicant: Covidien LP, Mansfield, MA (US)

(72) Inventors: David Farascioni, Bethel, CT (US); Dino Kasvikis, Mansfield, MA (US); Jonathan W. Sapienza, Orange, CT (US); Russell Estrella, Hamden, CT (US)

(73) Assignee: Covidien LP, Mansfield, MA (US)

( * ) Notice: Subject to any disclaimer, the term of this patent is extended or adjusted under 35 U.S.C. 154(b) by 773 days.

This patent is subject to a terminal disclaimer.

(21) Appl. No.: 13/854,551

(22) Filed: Apr. 1, 2013

(65) Prior Publication Data

US 2013/0231643 A1    Sep. 5, 2013

Related U.S. Application Data

(63) Continuation of application No. 13/532,955, filed on Jun. 26, 2012, now Pat. No. 8,418,906, which is a continuation of application No. 12/609,655, filed on Oct. 30, 2009, now Pat. No. 8,225,979.

(51) Int. Cl.
| | |
|---|---|
| *A61B 19/00* | (2006.01) |
| *A61B 17/068* | (2006.01) |
| *A61B 17/072* | (2006.01) |
| *A61B 17/00* | (2006.01) |

(52) U.S. Cl.
CPC ......... *A61B 19/00* (2013.01); *A61B 17/07207* (2013.01); *A61B 90/00* (2016.02); *A61B 2017/0046* (2013.01); *A61B 2017/00473* (2013.01); *A61B 2017/07221* (2013.01); *A61B 2017/07271* (2013.01); *A61B 2090/038* (2016.02)

(58) Field of Classification Search
CPC .............. A61B 2019/308; A61B 2017/07271; A61B 2019/4805; A61B 2019/4873; A61B 17/068; A61B 2017/0688
USPC ................................ 227/175.1, 175.4, 176.1
See application file for complete search history.

(56) References Cited

U.S. PATENT DOCUMENTS

| | | |
|---|---|---|
| 3,017,637 A | 1/1962 | Sampson |
| 3,079,306 A | 2/1963 | Bobrov et al. |

(Continued)

FOREIGN PATENT DOCUMENTS

| | | |
|---|---|---|
| CN | 101156792 A | 4/2008 |
| DE | 4300307 | 7/1994 |

(Continued)

OTHER PUBLICATIONS

Chinese Office Action issued in corresponding Chinese Appln. No. 201410390035.0 dated Dec. 1, 2015.

(Continued)

*Primary Examiner* — Michelle Lopez

(57) ABSTRACT

A locking shipping wedge is provided and generally includes a body portion having an elongate transverse member projecting from the body portion which is engageable with a drive assembly of a loading unit. A locking mechanism is provided on the body portion of the shipping wedge which is engageable with locking structure movably mounted within the loading unit.

7 Claims, 21 Drawing Sheets

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,499,591 A | 3/1970 | Green |
| 4,244,372 A | 1/1981 | Kapitanov et al. |
| 4,429,695 A | 2/1984 | Green |
| 4,520,817 A | 6/1985 | Green |
| 4,576,167 A | 3/1986 | Noiles |
| 4,589,413 A | 5/1986 | Malyshev et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,664,305 A | 5/1987 | Blake et al. |
| 4,672,964 A | 6/1987 | Dee et al. |
| 4,715,520 A | 12/1987 | Roehr, Jr. et al. |
| 4,763,669 A | 8/1988 | Jaeger |
| 4,819,853 A | 4/1989 | Green |
| 4,863,088 A | 9/1989 | Redmond et al. |
| 4,880,015 A | 11/1989 | Nierman |
| 4,881,544 A | 11/1989 | Green et al. |
| 4,892,244 A | 1/1990 | Fox et al. |
| 4,924,864 A | 5/1990 | Danzig |
| 4,978,049 A | 12/1990 | Green |
| 4,991,764 A | 2/1991 | Mericle |
| 5,014,899 A | 5/1991 | Presty et al. |
| 5,040,715 A | 8/1991 | Green et al. |
| 5,065,929 A | 11/1991 | Schulze et al. |
| 5,071,052 A | 12/1991 | Rodak et al. |
| 5,071,430 A | 12/1991 | De Salis et al. |
| 5,074,454 A | 12/1991 | Peters |
| 5,083,695 A | 1/1992 | Foslien et al. |
| 5,104,025 A | 4/1992 | Main et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,144,942 A | 9/1992 | Decarie et al. |
| 5,152,279 A | 10/1992 | Wilk |
| 5,156,315 A | 10/1992 | Green et al. |
| 5,180,092 A | 1/1993 | Crainich |
| 5,209,747 A | 5/1993 | Knoepfler |
| 5,275,608 A | 1/1994 | Forman et al. |
| 5,282,826 A | 2/1994 | Quadri |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,350,391 A | 9/1994 | Iacovelli |
| 5,354,311 A | 10/1994 | Kambin et al. |
| 5,358,506 A | 10/1994 | Green et al. |
| 5,366,133 A | 11/1994 | Geiste |
| 5,366,477 A | 11/1994 | LeMarie, III et al. |
| 5,374,277 A | 12/1994 | Hassler |
| 5,376,095 A | 12/1994 | Ortiz |
| 5,379,933 A | 1/1995 | Green et al. |
| 5,383,888 A | 1/1995 | Zvenyatsky et al. |
| 5,389,098 A | 2/1995 | Tsuruta et al. |
| 5,397,046 A | 3/1995 | Savage et al. |
| 5,397,324 A | 3/1995 | Carroll et al. |
| 5,403,312 A | 4/1995 | Yates et al. |
| 5,413,268 A | 5/1995 | Green et al. |
| 5,415,334 A | 5/1995 | Williamson, IV et al. |
| 5,415,335 A | 5/1995 | Knodell, Jr. |
| 5,423,471 A | 6/1995 | Mastri et al. |
| 5,433,721 A | 7/1995 | Hooven et al. |
| 5,452,837 A | 9/1995 | Williamson, IV et al. |
| 5,465,895 A | 11/1995 | Knodel et al. |
| 5,467,911 A | 11/1995 | Tsuruta et al. |
| 5,470,008 A | 11/1995 | Rodak |
| 5,474,566 A | 12/1995 | Alesi et al. |
| 5,474,571 A | 12/1995 | Lang |
| 5,484,451 A | 1/1996 | Akopov et al. |
| 5,486,185 A | 1/1996 | Freitas et al. |
| 5,487,500 A | 1/1996 | Knodel et al. |
| 5,507,426 A | 4/1996 | Young et al. |
| 5,535,935 A | 7/1996 | Vidal et al. |
| 5,551,622 A | 9/1996 | Yoon |
| 5,562,241 A | 10/1996 | Knodel et al. |
| 5,582,617 A | 12/1996 | Klieman et al. |
| 5,597,107 A | 1/1997 | Knodel et al. |
| 5,601,573 A | 2/1997 | Fogelberg et al. |
| 5,605,272 A | 2/1997 | Witt et al. |
| 5,630,539 A | 5/1997 | Plyley et al. |
| 5,634,584 A | 6/1997 | Okorocha et al. |
| 5,651,491 A | 7/1997 | Heaton et al. |
| 5,653,373 A | 8/1997 | Green et al. |
| 5,655,698 A | 8/1997 | Yoon |
| 5,662,258 A | 9/1997 | Knodel et al. |
| 5,662,259 A | 9/1997 | Yoon |
| 5,662,260 A | 9/1997 | Yoon |
| 5,673,841 A | 10/1997 | Schulze et al. |
| 5,680,982 A | 10/1997 | Schulze et al. |
| 5,681,330 A | 10/1997 | Hughett et al. |
| 5,715,988 A | 2/1998 | Palmer |
| 5,718,359 A | 2/1998 | Palmer et al. |
| 5,762,255 A | 6/1998 | Chrisman et al. |
| 5,794,834 A | 8/1998 | Hamblin et al. |
| 5,797,537 A | 8/1998 | Oberlin et al. |
| 5,800,449 A | 9/1998 | Wales |
| 5,816,471 A | 10/1998 | Plyley et al. |
| 5,820,009 A | 10/1998 | Melling et al. |
| 5,893,506 A | 4/1999 | Powell |
| 5,901,895 A | 5/1999 | Heaton et al. |
| 5,911,352 A | 6/1999 | Racenet et al. |
| 5,984,938 A | 11/1999 | Yoon |
| 5,988,479 A | 11/1999 | Palmer |
| 5,993,465 A | 11/1999 | Shipp et al. |
| 6,010,054 A | 1/2000 | Johnson et al. |
| 6,032,849 A | 3/2000 | Mastri et al. |
| 6,050,472 A | 4/2000 | Shibata |
| 6,079,606 A | 6/2000 | Milliman et al. |
| 6,109,500 A | 8/2000 | Alli et al. |
| 6,119,913 A | 9/2000 | Adams et al. |
| 6,131,789 A | 10/2000 | Schulze et al. |
| 6,174,309 B1 | 1/2001 | Wrublewski et al. |
| 6,241,139 B1 | 6/2001 | Milliman et al. |
| 6,241,140 B1 | 6/2001 | Adams et al. |
| 6,601,749 B2 | 8/2003 | Sullivan et al. |
| 6,607,540 B1 | 8/2003 | Shipp |
| 6,755,338 B2 | 6/2004 | Hahnen et al. |
| 6,805,273 B2 | 10/2004 | Bilotti et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,055,731 B2 | 6/2006 | Shelton, IV et al. |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,278,563 B1 | 10/2007 | Green |
| RE40,237 E | 4/2008 | Bilotti |
| 7,380,696 B2 | 6/2008 | Shelton, IV et al. |
| 7,407,078 B2 | 8/2008 | Shelton, IV et al. |
| 7,434,717 B2 | 10/2008 | Shelton, IV et al. |
| 7,451,904 B2 | 11/2008 | Shelton, IV |
| 7,464,849 B2 | 12/2008 | Shelton, IV et al. |
| 7,503,474 B2 | 3/2009 | Hillstead et al. |
| 7,568,604 B2 | 8/2009 | Ehrenfels et al. |
| 8,225,979 B2 * | 7/2012 | Farascioni ....... A61B 17/07207 227/175.1 |
| 2003/0050571 A1 | 3/2003 | Zarins et al. |
| 2005/0070758 A1 | 3/2005 | Wells et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2005/0184124 A1 | 8/2005 | Scirica et al. |
| 2005/0247752 A1 | 11/2005 | Kelly et al. |
| 2005/0247753 A1 | 11/2005 | Kelly et al. |
| 2005/0288606 A1 | 12/2005 | Alter |
| 2006/0144898 A1 | 7/2006 | Bilotti et al. |

(56) References Cited

U.S. PATENT DOCUMENTS

| | | |
|---|---|---|
| 2006/0226195 A1* | 10/2006 | Scirica ............. A61B 17/07207 227/175.1 |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0114261 A1 | 5/2007 | Ortiz et al. |
| 2007/0175950 A1 | 8/2007 | Shelton, IV et al. |
| 2007/0181631 A1 | 8/2007 | Bilotti et al. |
| 2007/0219563 A1 | 9/2007 | Voegele |
| 2007/0221702 A1 | 9/2007 | Kruszynski |
| 2007/0246508 A1 | 10/2007 | Green |
| 2007/0255296 A1 | 11/2007 | Sauer |
| 2008/0027466 A1 | 1/2008 | Vitali et al. |
| 2008/0093415 A1 | 4/2008 | Bilotti |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0272171 A1 | 11/2008 | Viola |
| 2008/0302854 A1 | 12/2008 | Rethy et al. |
| 2009/0008424 A1 | 1/2009 | Green |
| 2009/0134199 A1 | 5/2009 | Heinrich et al. |
| 2009/0206131 A1 | 8/2009 | Weisenburgh, II et al. |
| 2009/0272784 A1 | 11/2009 | Farascioni |
| 2010/0072258 A1 | 3/2010 | Farascioni et al. |

FOREIGN PATENT DOCUMENTS

| | | |
|---|---|---|
| DE | 20217850 | 1/2003 |
| EP | 0484677 | 5/1992 |
| EP | 0537498 | 4/1993 |
| EP | 0589306 | 3/1994 |
| EP | 0591946 | 4/1994 |
| EP | 0592243 | 4/1994 |
| EP | 0600182 | 6/1994 |
| EP | 0621009 | 10/1994 |
| EP | 0656188 | 6/1995 |
| EP | 1550410 | 7/2005 |
| EP | 1908413 | 4/2008 |
| FR | 2681775 | 10/1991 |
| WO | WO 03/022133 | 3/2003 |

OTHER PUBLICATIONS

European Search Report in EP 11250770 dated Mar. 1, 2012.
European Search Report in EP 11178544 dated Sep. 29, 2011.
European Search Report in EP 10251882 dated Feb. 17, 2011.
Australian Office Action for Australian Appln. No. 2014216031 dated Jul. 14, 2015.
Japanese Official Action from Appl. No. 2010-235958 dated Sep. 1, 2015.
Canadian Office Action dated Jun. 13, 2016, issued in Canadian Application No. 2,719,580.

* cited by examiner

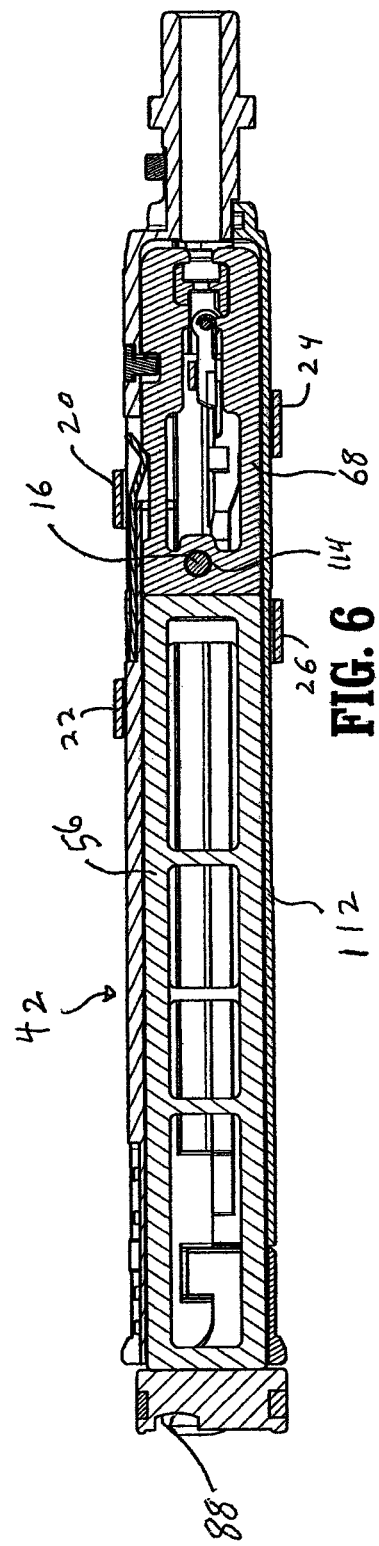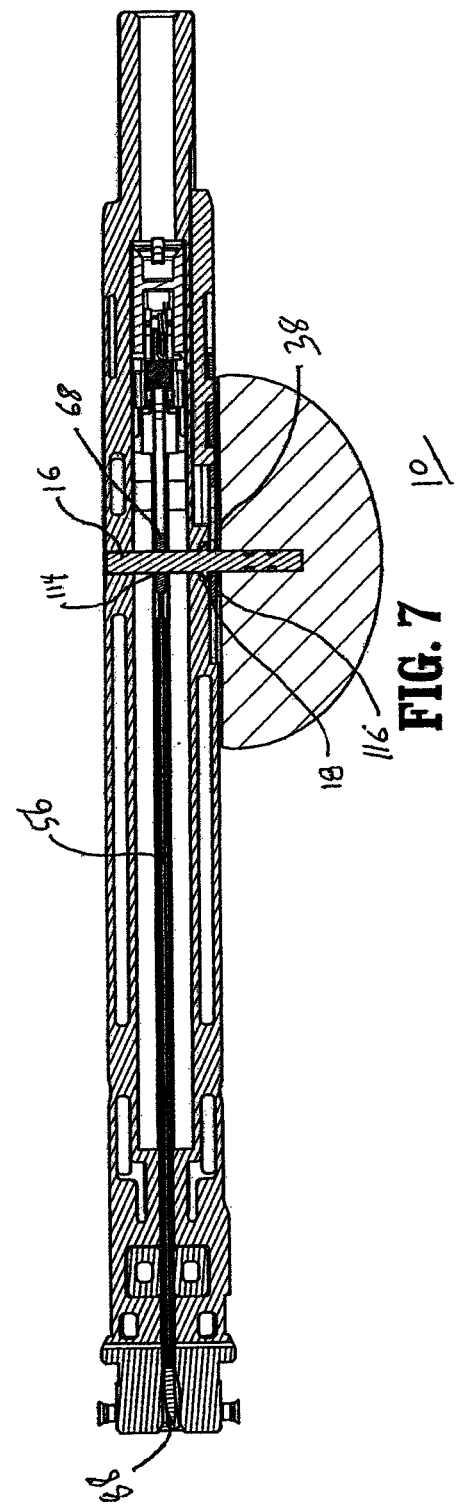

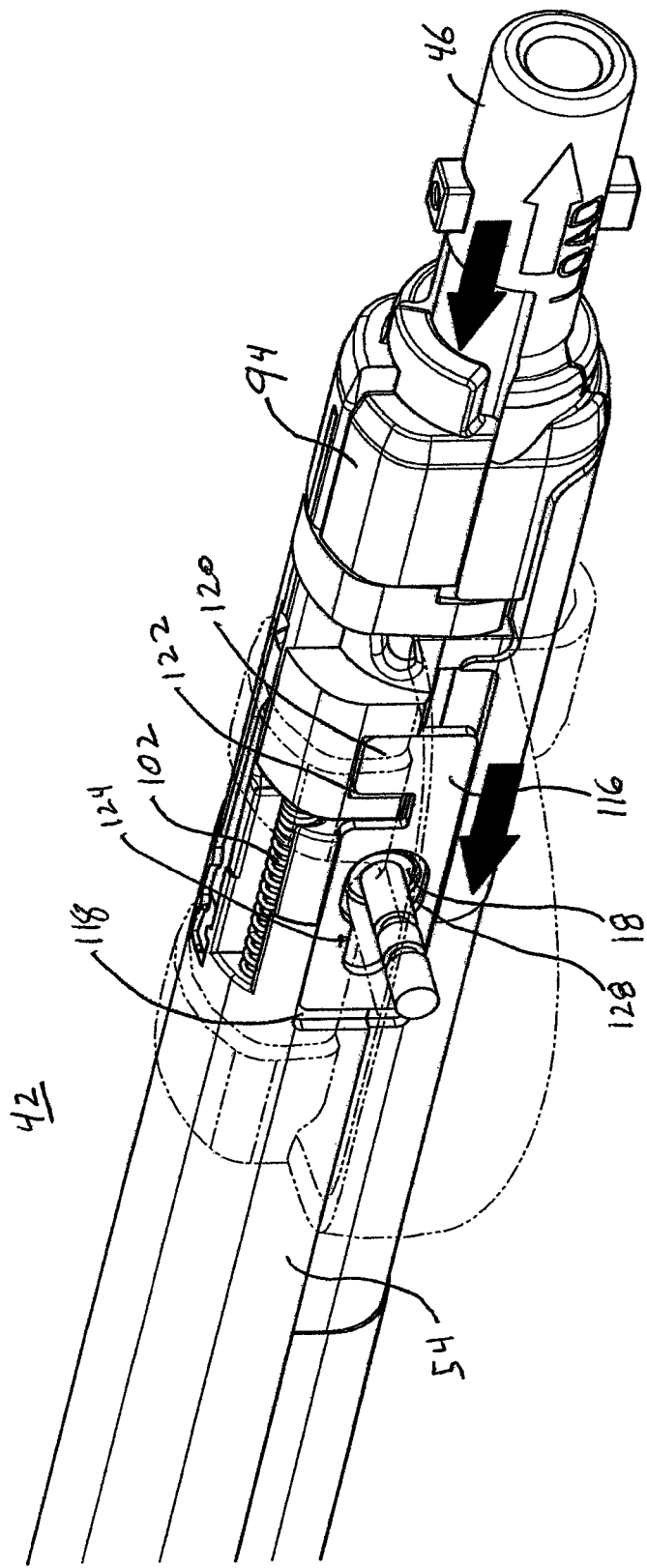

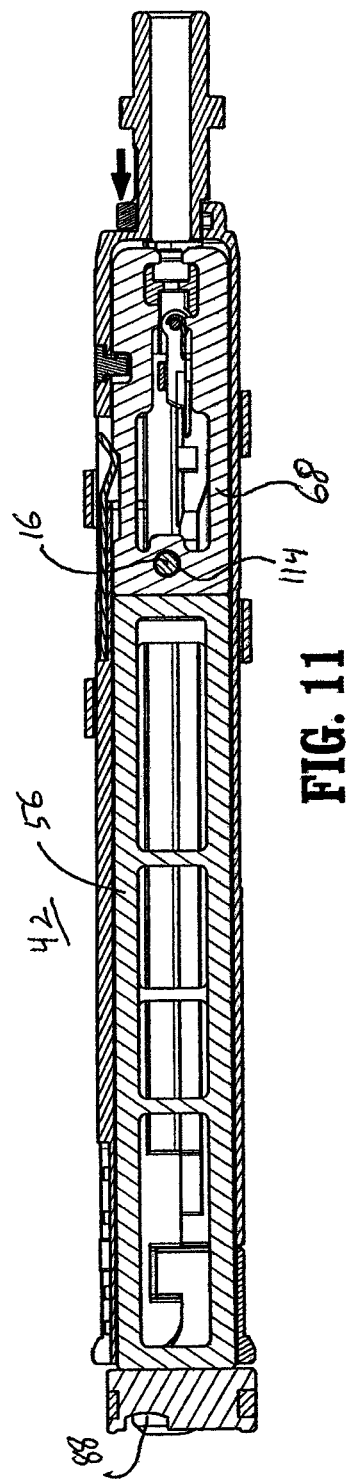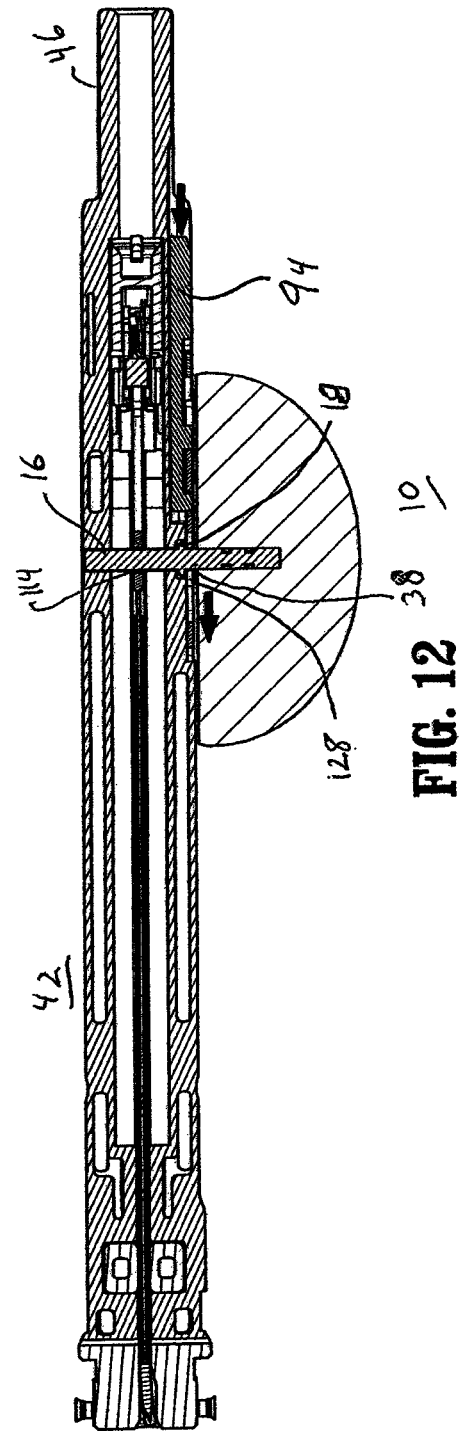

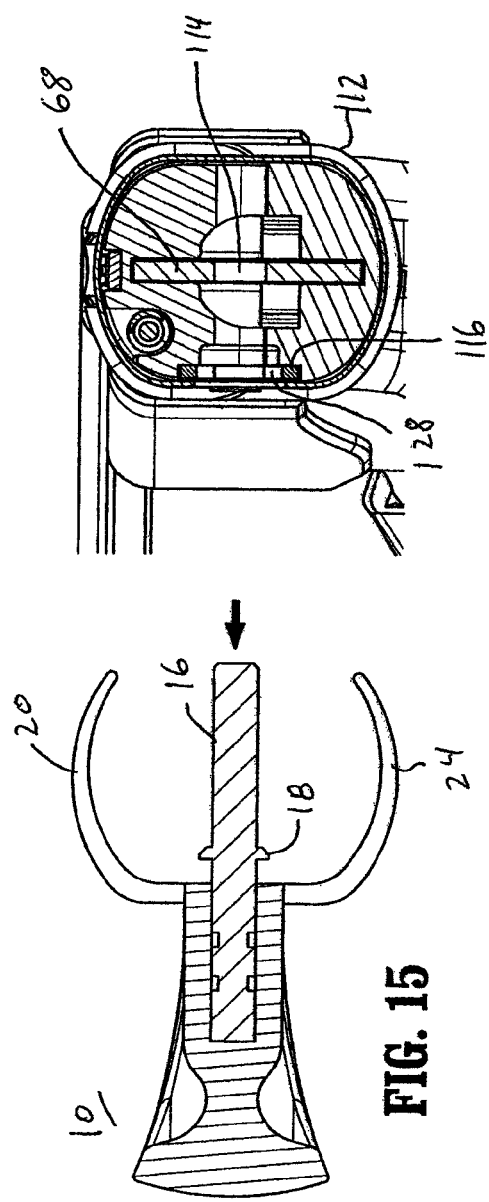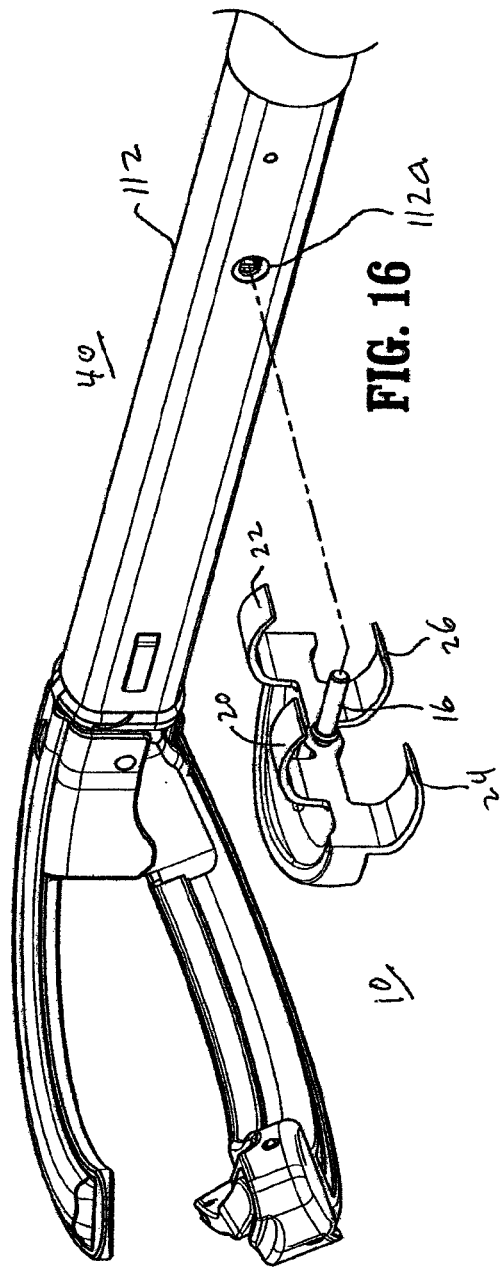
FIG. 15
FIG. 16

LOCKING SHIPPING WEDGE

CROSS-REFERENCE TO RELATED APPLICATIONS

This application is a continuation of U.S. patent application Ser. No. 13/532,955, filed Jun. 26, 2012, now U.S. Pat. No. 8,418,906, which is a continuation of U.S. patent application Ser. No. 12/609,655, filed Oct. 30, 2009, now U.S. Pat. No. 8,225,979, and the disclosures of each of the above-identified applications are hereby incorporated by reference in their entirety.

BACKGROUND

1. Technical Field

The present disclosure relates to a locking shipping wedge for use with a single use loading unit ("SULU") of a surgical instrument. More particularly, the present disclosure relates to a locking shipping wedge that immobilizes a drive assembly of a surgical instrument and a locking mechanism to prevent removal of the locking shipping wedge.

2. Background of Related Art

Various surgical procedures are performed with surgical instruments having disposable or replaceable loading units, e.g., SULU's. These loading units generally include a movable part or parts positioned to engage a drive member of a surgical instrument. If the moving part is not properly retained in position prior to and during attachment of the loading unit to a surgical instrument, the loading unit may not properly engage the surgical instrument and, thus, may not function properly. Some surgical instruments are provided with automatic locking systems which block movement of the components of the tool assembly prior to attachment to a surgical instrument and allow for free movement of the movable parts of the tool assembly once the loading unit has been properly positioned on the surgical instrument.

It would be desirable to provide a locking shipping device for a loading unit which prevents movement of the internal parts of the loading unit prior to attachment of the loading unit to a surgical instrument. It would also be desirable to provide a mechanism to prevent manual removal of the locking shipping device from the loading unit until the loading unit has been attached to the surgical instrument to prevent misalignment of the components of the loading unit with the surgical instrument.

SUMMARY

A loading unit and shipping wedge assembly is disclosed which includes a loading unit adapted to releasably engage a surgical instrument and a shipping wedge. The loading unit includes a tool assembly and a drive assembly which is movable from a retracted position to an advanced position to actuate the tool assembly. The shipping wedge is configured to releasably engage the loading unit and includes a transverse member positioned to extend into the loading unit and engage the drive member to retain the drive member of the loading unit in the retracted position. In one embodiment, the transverse member includes a pin and the drive assembly includes a hole dimensioned to receive the pin.

In one embodiment, the transverse member includes a flange and a lock plate is slidably supported within the loading unit. The lock plate defines a keyhole including a locking portion and a release portion. The keyhole is dimensioned to receive the transverse member. The flange portion is dimensioned to restrict passage of the transverse member through the locking portion of the keyhole but to permit passage of the transverse member through the release portion of the keyhole. The lock plate is movable from a first position in which the locking portion of the keyhole is aligned with the transverse member to prevent separation of the shipping wedge from the loading unit to a second position in which the release portion of the keyhole is aligned with the transverse member to permit separation of the shipping wedge from the loading unit. In one embodiment, the lock plate is adapted to be moved from the first position to the second position in response to engagement of the loading unit with a surgical instrument.

The shipping wedge may include at least one pair of flexible clips configured to be releasably positioned about the loading unit. The shipping wedge may also include a body defining at least one dish portion to facilitate grasping of the shipping wedge.

In one embodiment, the loading unit includes a tab which is movable from a first position to a second position and the shipping wedge includes a locking lip which is aligned with the tab when the tab is in its first position to prevent separation of the shipping wedge from the loading unit and is misaligned with the tab when the tab is moved to the second position to permit separation of the shipping wedge from the loading unit. The tab can be adapted to be moved from the first position to the second position in response to attachment of the loading unit to a surgical instrument.

A shipping wedge for use with a loading unit of a surgical instrument is disclosed which includes a body portion and an elongate transverse member extending from the body portion. The elongate transverse member is configured and dimensioned to be engageable with a drive assembly of a loading unit to prevent linear movement of the drive assembly. A locking member is releasably engageable with the loading unit to prevent removal of the transverse member from the loading unit. In one embodiment, the locking member includes a flange formed on the elongate transverse member. Alternatively, the locking member may include a lip projecting from the body portion. The lip can project from a plate affixed to the body portion. The elongate transverse member may also extend from the plate.

In one embodiment, the shipping wedge includes at least one upper clip and one lower clip frictionally engageable with the loading unit.

A shipping wedge for use with a loading unit of a surgical instrument is also disclosed which includes a body portion and an elongate transverse member extending from the body portion. The elongate transverse member can be positioned and configured to be engageable with a drive assembly of a loading unit. The shipping wedge also includes a locking mechanism for releasably retaining the elongate transverse member within the loading unit to prevent removal of the transverse member from the loading unit. The locking mechanism can include a flange formed on the elongate transverse member and a lock plate movably mounted within the loading unit.

In one embodiment, the lock plate includes a keyhole slot having a first portion preventing passage of the flange and a second enlarged portion allowing passage of the flange. Alternatively, the locking mechanism includes a lip projecting from the body portion which is positioned to be engageable with a tab movably mounted within the loading unit.

DESCRIPTION OF THE DRAWINGS

Various embodiments of the presently disclosed locking shipping wedge are disclosed herein with reference to the drawings, wherein:

FIG. 6 is a cross-sectional view taken along line 6-6 of FIG. 3;

FIG. 7 is a cross-sectional view taken along line 7-7 of FIG. 3;

FIG. 10 is a perspective view, similar to FIG. 5, during insertion of the proximal body portion into a surgical stapling instrument (not shown) and movement of the locking mechanism to the unlocked position;

FIG. 11 is a side view of the proximal body portion and locking shipping wedge, shown in section, in the unlocked position;

FIG. 12 is a top view of the proximal body portion and locking shipping wedge, shown in section, in the unlocked position;

FIG. 15 is a cross sectional view of the locking shipping wedge and proximal body portion illustrating removal of the locking shipping wedge from the proximal body portion;

FIG. 16 is a perspective view of the single use loading unit and locking shipping wedge illustrating removal of the locking shipping wedge from the single use loading unit;

DETAILED DESCRIPTION OF EMBODIMENTS

Embodiments of the presently disclosed locking shipping wedge including a locking mechanism will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
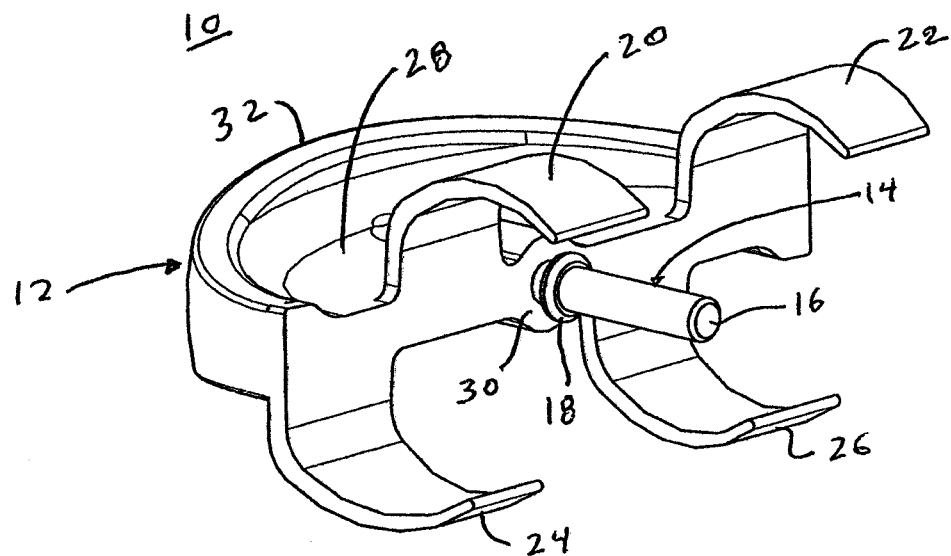
FIG. 1 is a frontal perspective view of one embodiment of a locking shipping wedge for use with a single use loading unit of a surgical stapling instrument.
Figure 2:
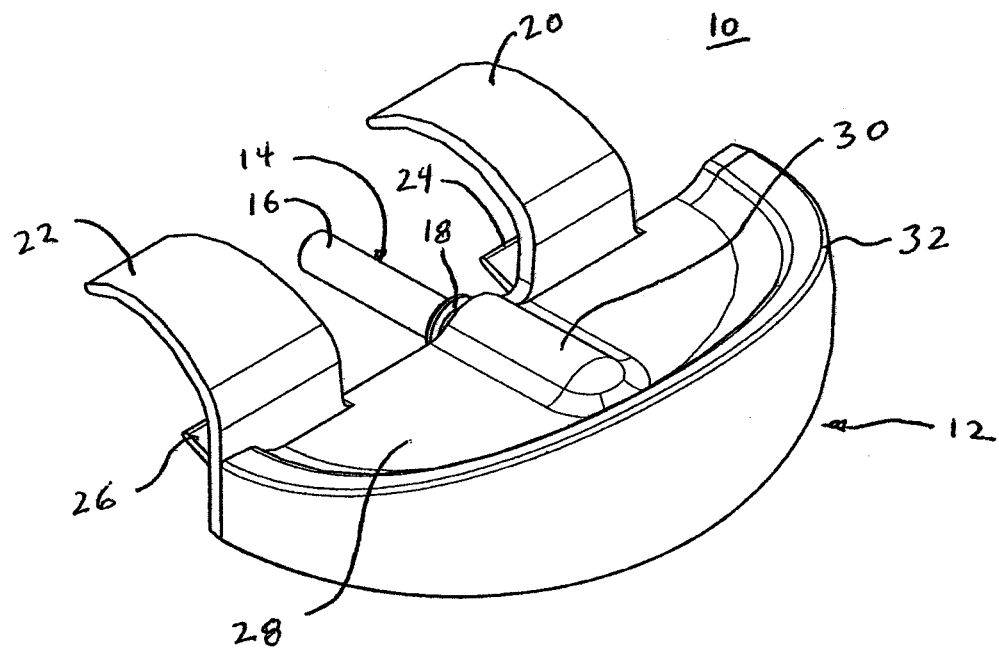
FIG. 2 is rearward perspective view of the locking shipping wedge of FIG. 1.

Referring to FIGS. 1 and 2, there is disclosed a locking shipping wedge or shipping wedge 10 for use with a loading unit of a surgical stapling instrument. Shipping wedge 10 is provided to prevent movement of a drive assembly of a loading unit prior to assembly of the loading unit with a surgical stapling instrument (not shown). Shipping wedge 10 generally includes a semicircular or dish shaped body portion 12 having a transverse pin 14 extending from body portion 12. Transverse pin 14 may be formed from a variety of materials such as, for example, metallic materials, polymeric materials, etc.

Transverse pin 14 includes an inner pin portion 16 which is provided to engage the drive assembly of a loading unit. A locking flange 18 is provided on transverse pin 14 and forms part of a locking mechanism, described in detail hereinbelow, to prevent removal of shipping wedge 10 from the loading unit until after the loading unit has been fixedly attached to a surgical stapling instrument. It should be noted that while locking flange 18 is disclosed as being circular, locking flange 18 may assume other configurations, such as rectangular or, triangular, etc. which conform with corresponding locking structure of a locking mechanism which is described in detail below.

A pair of flexible upper clips 20 and 22 and a pair of longitudinally offset, flexible lower clips 24 and 26 extend from body portion 12 and are configured to releasably engage the loading unit to support and stabilize shipping wedge 10 on the loading unit. As shown, body portion 12 includes an upper dish portion 28, a central tube 30 and an upper peripheral lip 32 surrounding upper dish portion 28. Central tube 30 is provided to receive and retain transverse pin 14 while upper peripheral lip 32 and upper dish portion 28 provide an ergonomic means of grasping shipping wedge 10. Alternatively, other ergonomic configurations are envisioned. Flexible upper clips 20 and 22 and flexible lower clips 24 and 26 are formed integrally with body portion 12. Upper and lower clips 20, 22 and 24, 26, respectively, along with body portion 12, may be formed from a variety of materials such as, for example, metallic materials, polymeric materials, etc.

Figure 2A:
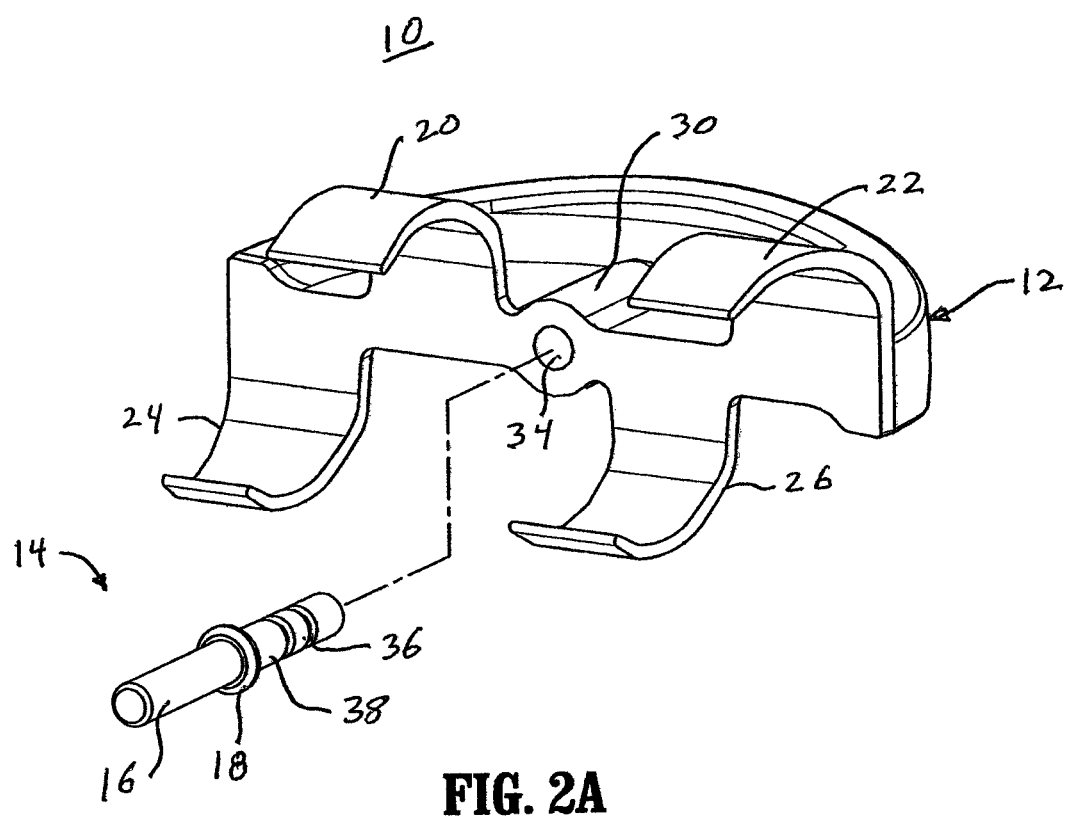
FIG. 2A is a perspective view of the locking shipping wedge of FIG. 1 with parts separated.

Referring to FIG. 2A, shipping wedge 10 includes a bore 34 formed through central tube 30 dimensioned to receive transverse pin 14. Specifically, transverse pin 14 includes an outer pin portion 36 which is fixedly secured within bore 34 in central tube 30. Outer pin portion 36 may be secured within bore 34 in any known manners such as, for example, welding, gluing, pinning etc. Alternatively, transverse pin 14 may be formed integrally with body portion 12 of shipping wedge 10. An intermediate portion 38 of pin 14 extends between locking flange 18 and outer portion 36 and is configured to move within a second component of the locking mechanism as described in more detail herein below.

Figure 3:
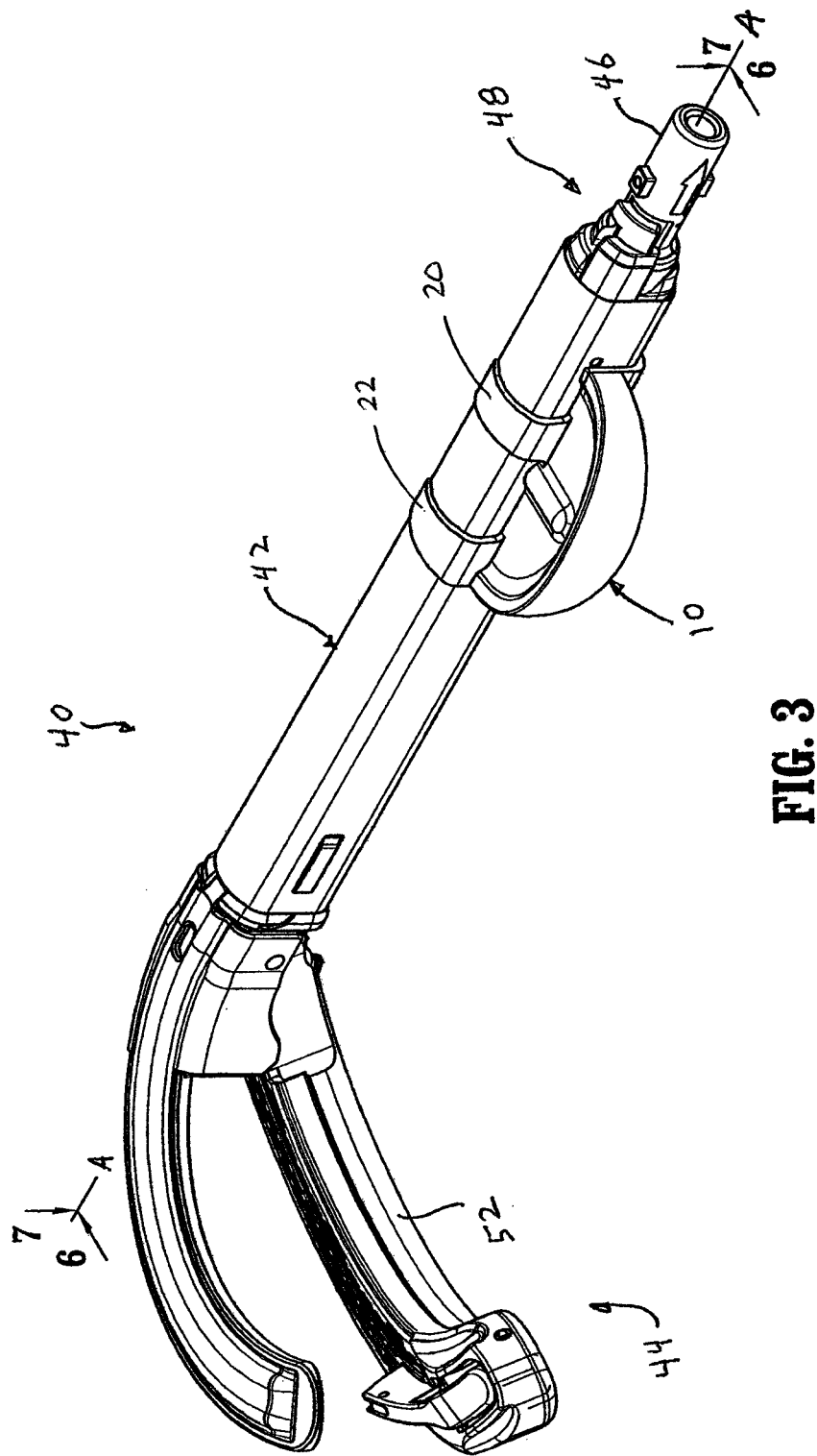
FIG. 3 is a perspective view of a single use loading unit for use with a surgical stapling instrument and incorporating the locking shipping wedge of FIG. 1.

Referring now to FIG. 3, loading unit 40 includes a proximal body portion 42 and a tool assembly 44. Proximal body portion 42 is releasably attachable to a distal end of an elongate body portion of a surgical stapling instrument (not shown) by means of an insertion tip 46 located at a proximal end 48 of proximal body portion 42. Tool assembly 44 includes an anvil assembly 50 and a cartridge assembly 52. Cartridge assembly 52 is pivotal in relation to anvil assembly 50 and is movable between an open or unclamped position and a closed or approximated position. In the embodiment shown, tool assembly 44 including anvil assembly 50 and cartridge assembly 52 is curved with respect to a longitudinal axis "A-A" of proximal body portion 42. Alternatively, tool assembly 44 may include a pair of linear jaws.

Figure 4:
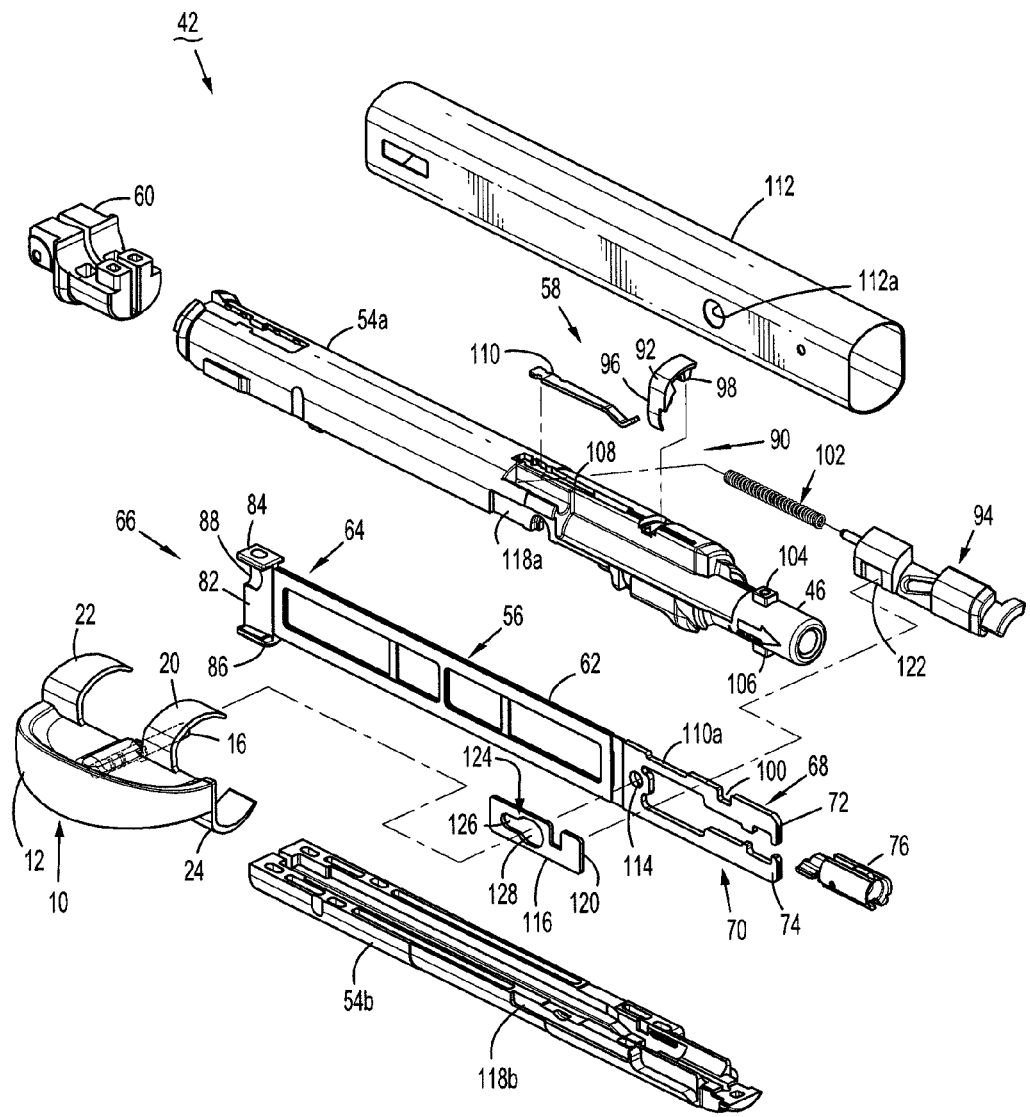
FIG. 4 is a perspective view, with parts separated, of a proximal body portion of the single use loading unit of FIG. 3.

With reference now to FIG. 4, proximal body portion 42 includes an inner body 54 formed from molded half sections 54a and 54b, a drive assembly 56 and a drive locking assembly 58. Proximal body portion 42 is coupled to tool assembly 44 by a mounting assembly 60 which is fixedly secured to inner body half section 54a.

Drive assembly 56 includes a flexible drive beam 62 which is sufficiently flexible to be advanced through the curvature of tool assembly 44. Alternatively, if the loading unit is of linear construction and includes an articulatable tool assembly, flexible drive beam 62 is sufficiently flexible to bend around the axis of articulation. Drive beam 62 has a distal end 64 which is secured to a dynamic clamping member 66, and a proximal engagement section 68. A proximal end 70 of engagement section 68 includes diametrically opposed inwardly extending fingers 72 and 74 which engage a hollow drive member 76 to fixedly secure drive member 76 to flexible drive beam 62. Drive member 76 defines a proximal porthole 80 which receives a distal end of a control rod (not shown) of a surgical instrument when loading unit 40 is attached to the surgical instrument.

Dynamic clamping member 66 includes a vertical strut 82, an upper beam 84 and a lower beam 86. A knife or cutting edge 88 is formed on vertical strut 82. When drive assembly 56 is advanced distally within tool assembly 44, upper beam 84 moves within anvil assembly 50 and lower beam 86 moves within cartridge assembly 52 to pivot cartridge assembly 52 from an open position to a closed position.

Loading unit 40 includes a locking mechanism 90 including a locking member 92 and a locking member actuator 94. Locking member 92 is movable from a first position, in which locking member 92 maintains drive assembly 56 in a prefered position, to a second position in which drive assembly 56 is free to move axially. Locking member 92 includes a semicylindrical body 96 which is slidably positioned in inner body half 54a of proximal body portion 42 of loading unit 40. Body 96 includes a radially inwardly extending finger 98 which is dimensioned to be received within a notch 100 formed in drive assembly 56. Engagement of finger 98 in notch 100 of drive assembly 56 prevents drive assembly 56 from moving linearly within proximal body portion 42 of loading unit 40 prior to attachment of loading unit 40 to a surgical instrument.

In use, prior to attachment of loading unit 40 onto a surgical stapling instrument, a spring 102 urges locking member actuator 94 proximally to a first position to maintain the lock member 92 in its first position wherein finger 98 of lock member 92 is received in notch 100 of drive assembly 56. When insertion tip 46 of loading unit 40 is linearly inserted into an open end of a body portion of a surgical stapling instrument (not shown), nubs 104 and 106 of insertion tip 46 move linearly through slots (not shown) formed in an open end of the body portion of the surgical stapling instrument. As loading unit 40 is moved further into the body portion, locking member actuator 94 is moved from its first position to its second position. As locking member actuator 94 engages the body portion of the surgical instrument and is moved against the bias of spring 102 to its second position, lock member 92 is cammed from its first position engaged with notch 100 of drive assembly 56 to its second position to move finger 98 from notch 100. This locking mechanism, including locking member 92 and a locking member actuator 94 prevents advancement of drive assembly 56 of loading unit 40 prior to engagement of loading unit 40 with a surgical stapling instrument.

Inner body half section 54a of proximal body portion 42 of loading unit 40 defines a longitudinal slot 108 which receives a leaf spring 110. Leaf spring 110 is confined within slot 108 by an outer sleeve 112 which is positioned about and receives half-sections 54a and 54b of inner body 54. Leaf spring 110 is received in a stepped portion 110a of drive assembly 56 to assist in retaining drive assembly 56 in its retracted position until loading unit 40 has been attached to a surgical instrument and the surgical instrument has been actuated. It should be noted that outer sleeve 112 is provided with a hole 112a for passage of transverse pin 14 of shipping wedge 10. When drive beam 62 is advanced distally, leaf spring 110 is flexed upwardly to permit distal movement of drive beam 62 of drive assembly 56.

An exemplary example of the loading unit is disclosed in U.S. patent/patent application Ser. No. 12/553,174, filed on Sep. 3, 2009 and entitled LOWER ANTERIOR RESECTION DEVICE, the entire contents of which are incorporated herein by reference.

Referring now to FIGS. 2A and 4, as noted hereinabove, flexible upper clips 20 and 22 and flexible lower clips 24 and 26 are provided to retain shipping wedge 10 on a loading unit 40 (FIG. 3). Specifically, flexible upper clips 20 and 22 and flexible lower clips 24 and 26 frictionally engage outer sleeve 112 of proximal body portion 42.

Shipping wedge 10 is provided to maintain drive assembly 56 in a retracted position to facilitate attachment of drive member 76 (FIG. 4) of loading unit 40 to a control rod of a surgical instrument. Specifically, inner pin portion 16 of shipping wedge 10 is configured to be received in a hole 114 (FIG. 4) formed in engagement section 68 of drive assembly 56 to prevent movement of drive assembly 56 until loading unit 40 has been attached to a surgical instrument.

As noted hereinabove, flange 18 on transverse pin 14 forms part of a locking mechanism which prevents removal of shipping wedge 10 from loading unit 40 until loading unit 40 has been properly engaged with a surgical stapling instrument.

Figure 5:
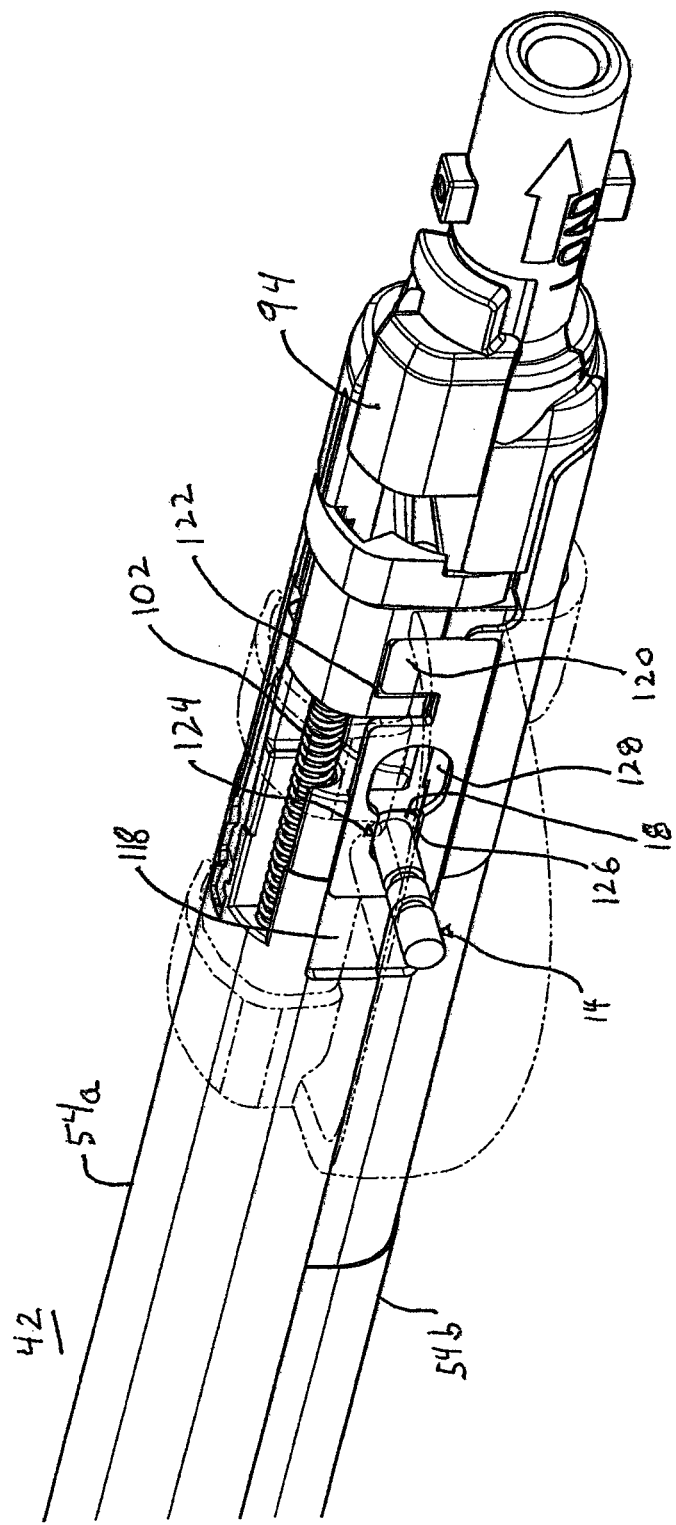
FIG. 5 is a perspective view of a proximal end of the proximal body portion illustrating a locking mechanism in a locked position with a portion of the locking shipping wedge shown in phantom and an outer sleeve removed.
Figure 8:
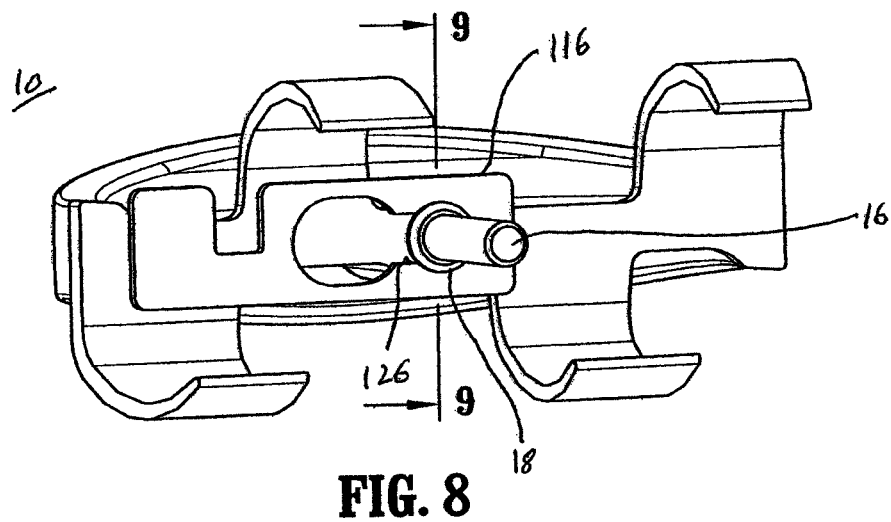
FIG. 8 is a perspective view of the locking shipping wedge incorporating the locking mechanism and in the locked position.

As best shown in FIGS. 4 and 5, the disclosed locking mechanism includes a lock plate 116 which is movably supported within a tray 118 (FIG. 5) formed in inner body halves 54a and 54b. Lock plate 116 is free to slide longitudinally within tray 118 and is held in place by outer sleeve 112 of proximal body portion 42. In order to move lock plate 116 within tray 118, lock plate 116 includes a proximal finger 120 which is engageable with a notch 122 formed in locking member actuator 94. Thus, as locking member actuator 94 is moved distally during engagement of loading unit 40 with a surgical suturing instrument, lock plate 116 is driven distally within tray 118.

In order to prevent removal of locking shipping wedge 10 from loading unit 40, lock plate 116 includes a keyhole slot 124 having a distally extending longitudinal lock slot 126 and an enlarged proximal release opening 128. Intermediate portion 38 of transverse pin 14 (FIG. 2A) rides within lock slot 126. Flange 18 of transverse pin 14 is larger in diameter than the width of lock slot 126 preventing flange 18 from being pulled through lock slot 126. However, release opening 128 of keyhole slot 124 is sufficiently large enough in diameter to allow passage of locking flange 18 and allow removal of locking shipping wedge 10 from loading unit 40.

Figure 9:
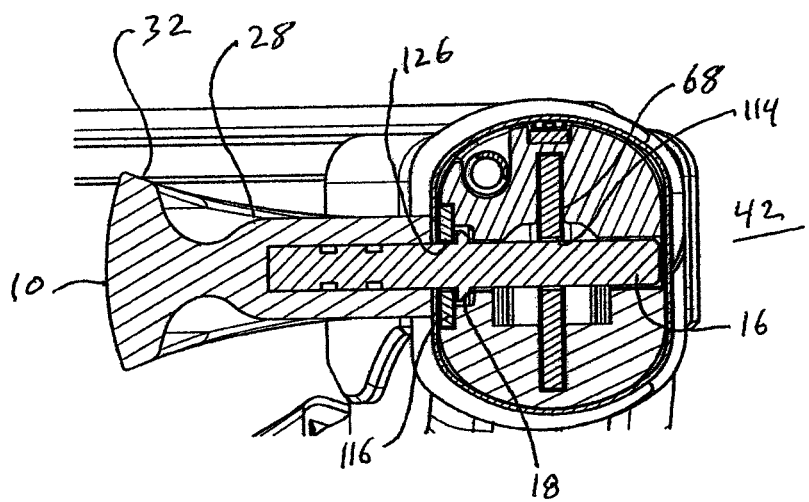
FIG. 9 is a cross-sectional view taken along line 9-9 of FIG. 8.

Referring now to FIGS. 5-9, and initially to FIGS. 6, 7 and 9, in the initial or locked condition, inner pin portion 16 of transverse pin 14 is positioned through hole 114 formed in proximal engagement section 68 of drive assembly 56. This immobilizes drive assembly 56 within proximal body portion 42 of loading unit 40 (FIGS. 6 and 7). Locking member actuator 94 is in a proximal position due to the bias of spring 102 (FIG. 5).

With reference to FIGS. 5, 7, 8 and 9, in the initial and locked condition, transverse pin 14, and thus intermediate pin portion 38 (FIG. 7), is located within lock slot 126 of keyhole slot 124 in lock plate 116. Thus, locking flange 18 is captured behind lock slot 126 thereby preventing removal of shipping wedge 10 from loading unit 40.

Figure 13:
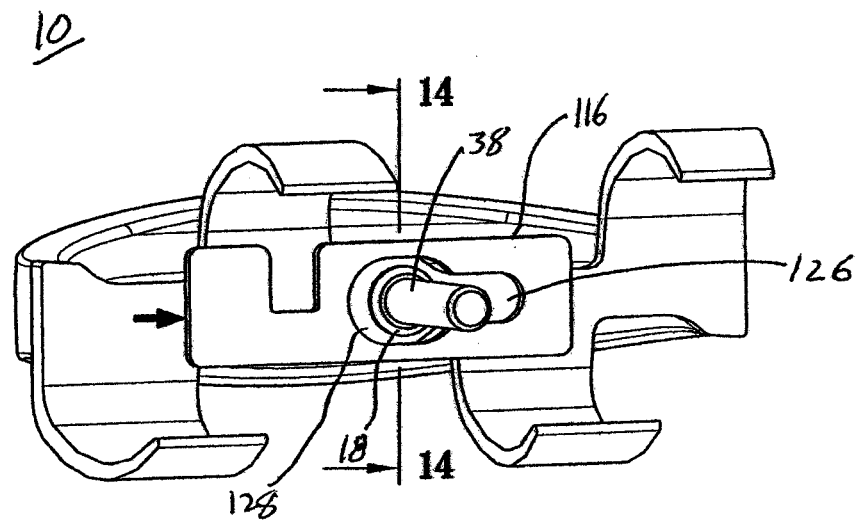
FIG. 13 is a perspective view of the locking shipping wedge incorporating the locking mechanism and in the unlocked position.
Figure 14:
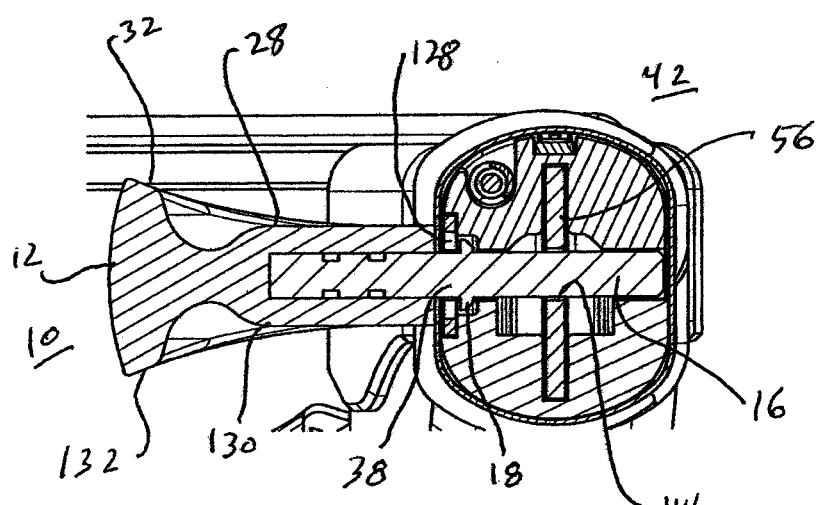
FIG. 14 is a cross sectional view taken along line 14-14 of FIG. 13.

Referring now to FIGS. 10-16, the disengagement of the locking mechanism and removal of shipping wedge 10 from proximal body portion 42 will now be described. With regard to FIGS. 10 and 12, when proximal body portion 42 is secured to the distal end of a surgical stapling instrument (not shown) by insertion of insertion tip 46 into an elongate tubular member of the surgical stapling instrument, the distal end of the elongate tubular member drives locking member actuator 94 distally against the bias of spring 102 (FIG. 10) and through proximal body portion 42. Movement of locking member actuator 94 distally forces locking plate 116 distally within tray 118 formed in inner body 54 thereby bringing locking flange 18 into alignment with release opening 128 in lock plate 116 (FIGS. 13 and 14).

In this position, locking shipping wedge 10 is now in the unlocked position and can be removed from proximal body portion 42 to withdraw inner pin portion 16 out of hole 114 of engagement section 68 of drive assembly thereby releasing drive assembly 56 for movement.

Referring specifically to FIG. 14, and as noted hereinabove, body portion 12 of locking shipping wedge 10 includes upper dish portion 28 and peripheral lip 32 to facilitate withdrawal of shipping wedge 10 from proximal body portion 42. To further assist removal, body portion 12 additionally includes a lower dish portion 130 surrounded by a lower peripheral lip 132. Referring to FIGS. 15 and 16, shipping wedge 10 is drawn sideways to disengage upper and lower clips 20 and 22 and 24 and 26, respectively, from outer sleeve 112. As locking shipping wedge 10 is withdrawn, transverse pin 14 is withdrawn through hole 112a in outer sleeve 112 and locking flange 18 is removed through release opening 128 in lock plate 116 to thereby draw inner pin portion 16 out of hole 114 in proximal engagement section 68 of drive assembly 56. Once shipping wedge 10 has been removed from loading unit 40, a surgical stapling instrument, connected to loading unit 40, may be actuated to perform a stapling procedure on tissue.

Figure 17:
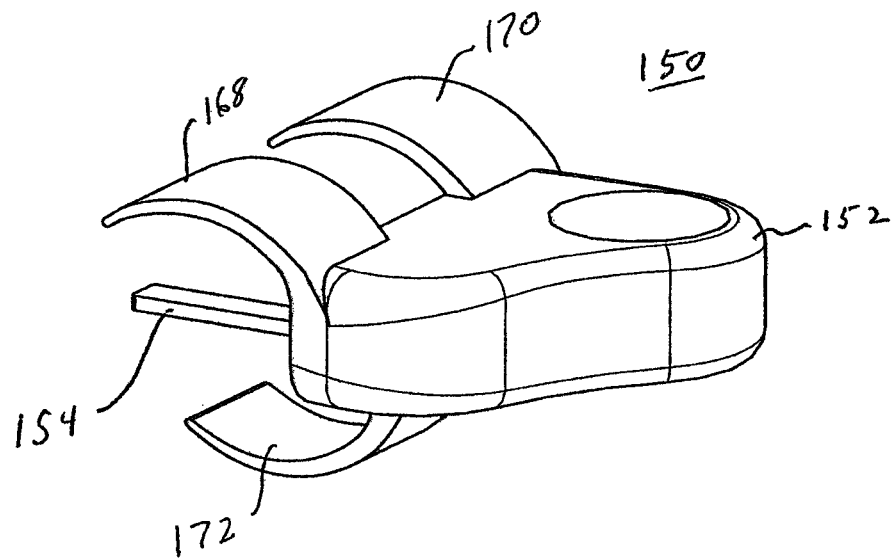
FIG. 17 is a frontal perspective view of another embodiment of a locking shipping wedge for use with a single use loading unit of a surgical stapling instrument.
Figure 18:
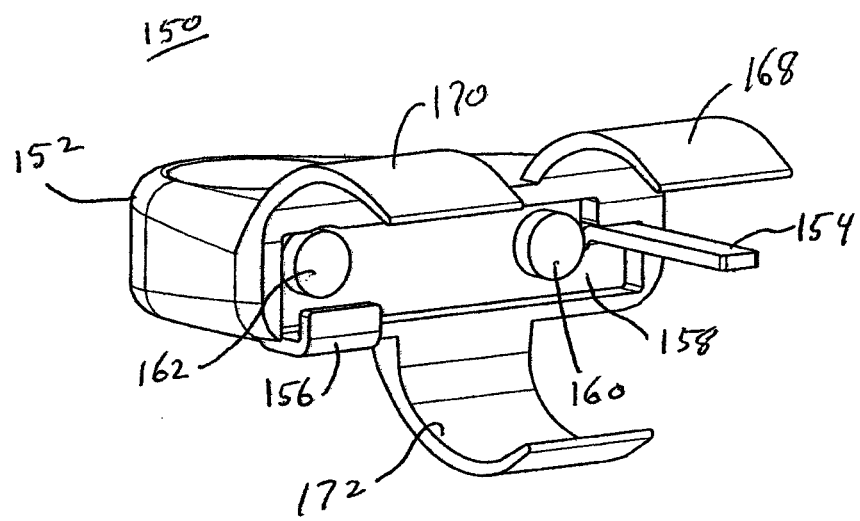
FIG. 18 is rearward perspective view of the locking shipping wedge of FIG. 17.
Figure 18A:
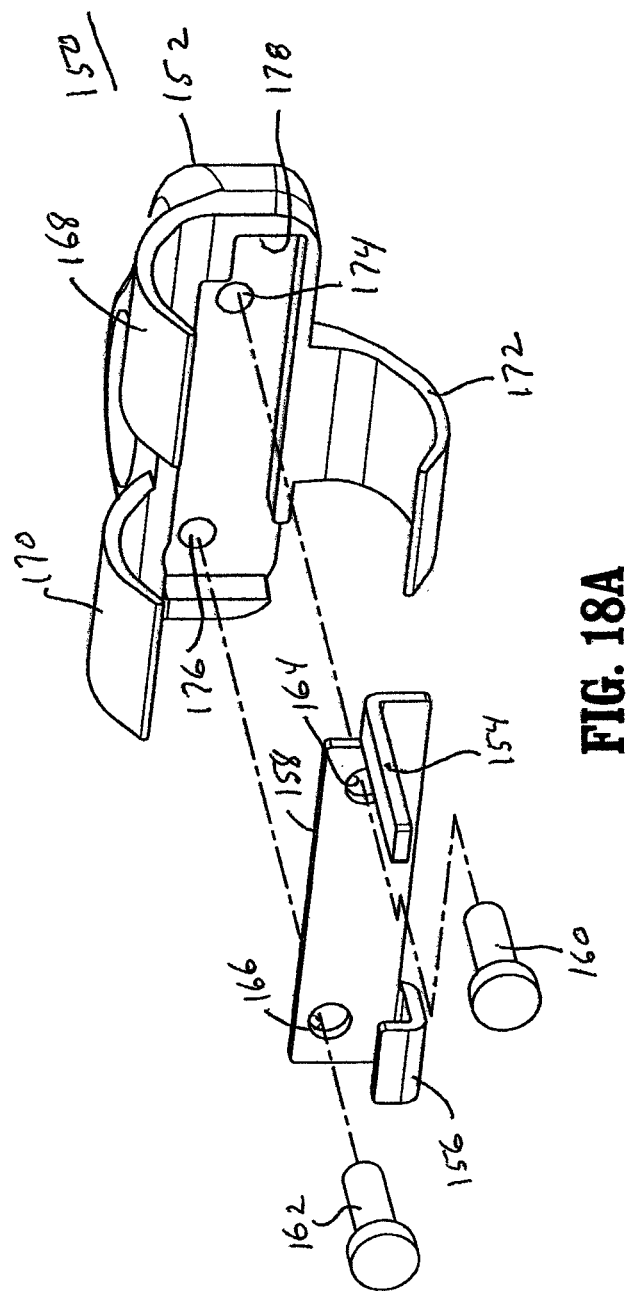
FIG. 18A is a perspective view of the locking shipping wedge of FIG. 17 with parts separated.

FIGS. 17-18A illustrate an alternative embodiment of a shipping wedge 150 having a body portion 152 and a transverse member 154 extending from body portion 152. An upwardly extending locking lip 156 is provided on body portion 152 to engage a component on a loading unit 180 (FIG. 18A) to form a locking mechanism to prevent locking shipping wedge 150 from being removed before the loading unit 180 has been fully engaged with a surgical stapling instrument. As best seen in FIGS. 18 and 18A, transverse member 154 and locking lip 156 extend from a support plate 158 which is affixed to body portion 152 by a pair of retention pins 160 and 162. With specific reference to FIG. 18A, pins 160 and 160 extend through holes 164 and 166 in support plate 158 and are configured to engage holes 174 and 176 in body portion 152. Support plate 158 is retained within a recess or tray 178 formed in a body portion 152 of loading unit 180.

Similar to shipping wedge 10 described hereinabove, shipping wedge 146 further includes a pair of flexible upper clips 168 and 170 and a flexible lower clip 172 extending from body portion 152. Flexible clips 168, 170 and 172 are provided to support and retain locking shipping wedge 150 on a loading unit 180 in a manner similar to that described hereinabove.

Figure 19:
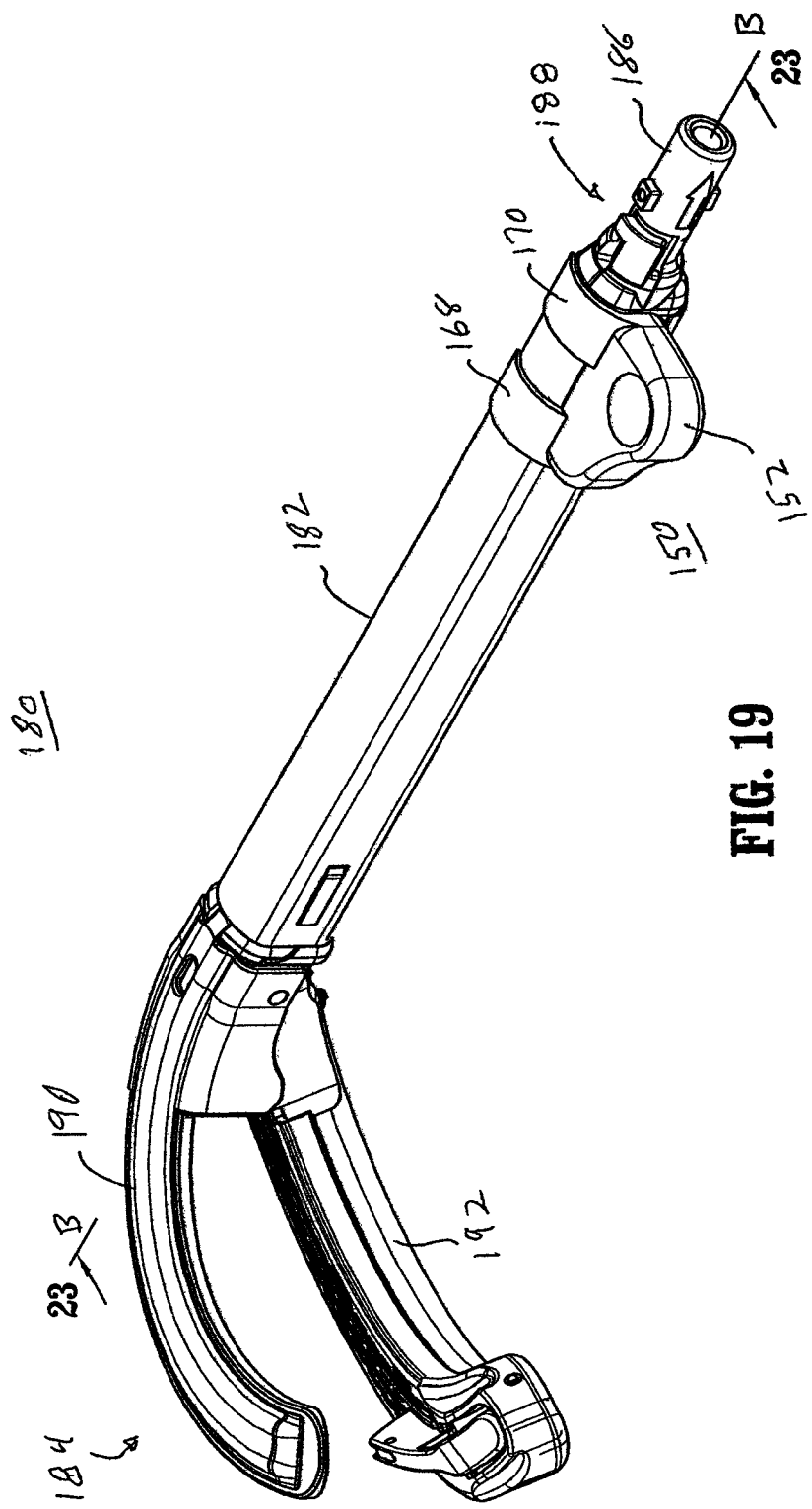
FIG. 19 is a perspective view of a single use loading unit for use with a surgical stapling instrument and incorporating the locking shipping wedge of FIG. 17.

Referring now to FIG. 19, loading unit 180 is substantially identical to loading unit 40 described hereinabove. Loading unit 180 generally includes a proximal body portion 182 and a tool assembly 184. Proximal body portion 182 is releasably attachable to a distal end of an elongated body portion of a surgical stapling instrument (not shown) by means of an insertion tip 186 formed at a proximal end 188 of body portion 182. Tool assembly 184 includes an anvil assembly 190 and a cartridge assembly 192. Cartridge assembly 192 is pivotal in relation to anvil assembly 190 and is movable between an open or unclamped position and a closed or approximated position. Tool assembly 184, which includes anvil assembly 190 and cartridge assembly 192, are curved with respect to a longitudinal axis "B-B" of proximal body portion. As discussed above, tool assembly 184 may also comprise linear jaws.

Figure 20:
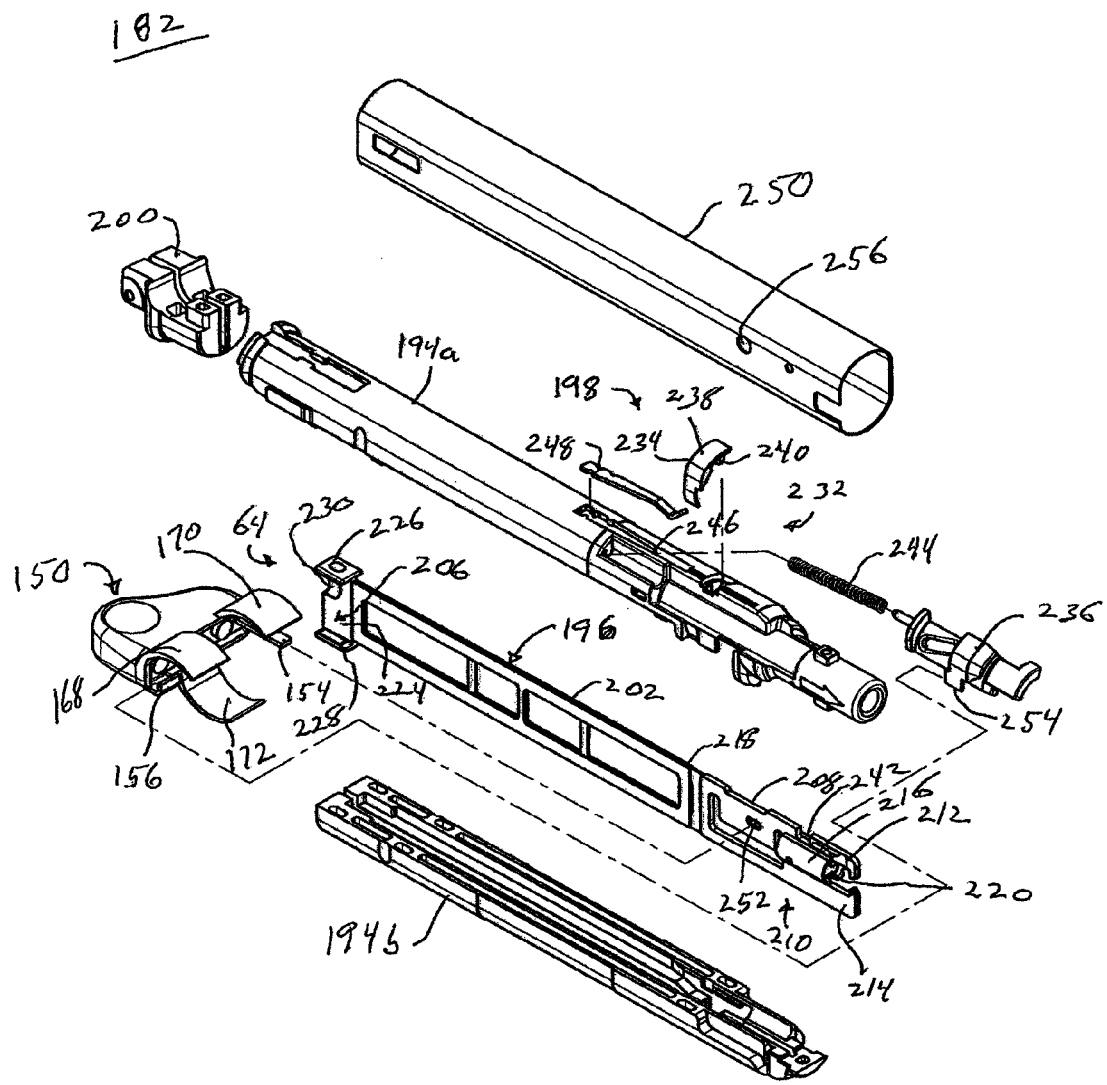
FIG. 20 is a perspective view, with parts separated, of a proximal body portion of the single use loading unit of FIG. 19.

With reference now to FIG. 20, proximal body portion 182 includes an inner body 194 formed from molded half sections 194a and 194b, a drive assembly 196 and a drive locking assembly 198. Proximal body portion 182 is coupled to tool assembly 184 by a mounting assembly 200. Mounting assembly 200 is fixedly secured to inner body half 194a.

Drive assembly 196 includes a flexible drive beam 202 which is sufficiently flexible to be advanced through the curvature of tool assembly when 184. Drive beam 202 has a distal end 204 which is secured to a dynamic clamping member 206, and a proximal engagement section 208. A proximal end 210 of engagement section 208 includes diametrically opposed inwardly extending fingers 212 and 214. Fingers 212 and 214 engage a hollow drive member 216 to fixedly secure drive member 216 to the proximal end 218 of flexible drive beam 202. Drive member 216 defines a proximal porthole 220 which receives the distal end of a control rod of a surgical instrument when loading unit 180 is attached to the surgical instrument.

Dynamic clamping member 206 includes a vertical strut 224, an upper beam 226 and a lower beam 228. A knife or cutting edge 230 is formed on vertical strut. When drive assembly 196 is advanced distally within tool assembly 184, upper beam 226 moves within anvil assembly 190 and lower beam 228 moves along cartridge assembly 192 to pivot cartridge assembly from an open position to a closed position.

Loading unit 180 includes a locking mechanism 232 including a locking member 234 and a locking member actuator 236. As discussed above with respect to lock member 92 and locking member actuator 94, locking member 236 is movable from a first position, in which locking member 236 maintains drive assembly 196 in a prefired position, to a second position in which drive assembly 196 is free to move axially. Locking member 234 includes a semicylindrical body 238 which is slidably positioned in inner body half 194a of body portion 194. Body 238 includes a radially inwardly extending finger 240 which is dimensioned to be received within a notch 242 formed in drive assembly 196. Engagement of finger 240 in notch 242 of drive assembly 196 prevents drive assembly 196 from moving linearly within body portion 194 to prevent actuation of loading unit 180 prior to attachment of loading unit 180 to a surgical stapling instrument.

A spring 244 is provided to urge actuator 236 to the first position to maintain lock member 234 in the first position as discussed above. Proximal body portion 182 functions substantially as described hereinabove with regard to loading unit 40 such that as proximal body portion 182 is moved into a body portion of a surgical stapling apparatus, locking member actuator 236 is moved from its first position to its second position.

Upper half section 194a of proximal body portion 182 defines a longitudinal slot 246 which receives a leaf spring 248. Leaf spring 248 is confined within slot 246 by an outer sleeve 250. When drive beam 202 is advanced distally, leaf spring 248 is flexed upwardly to permit distal movement of drive beam 202.

As noted hereinabove, shipping wedge 150 is configured to engage proximal body portion 182. Specifically, clips 168, 170 and 172 are configured to frictionally engage outer sleeve 250. In order to prevent movement of drive assembly 196 proximal engagement section 208 includes a slot 252 for receipt of transverse member 154 of shipping wedge 150.

In order to retain and release locking shipping wedge 150 from proximal body portion 182, locking member actuator 236 is provided with a downwardly projecting tab 254 which is configured to engage upwardly projecting lip 156 on shipping wedge 150. It should be noted that a hole 256 is provided through outer sleeve 250 to allow for passage of transverse member of 154 into proximal body portion 182.

Figure 21:
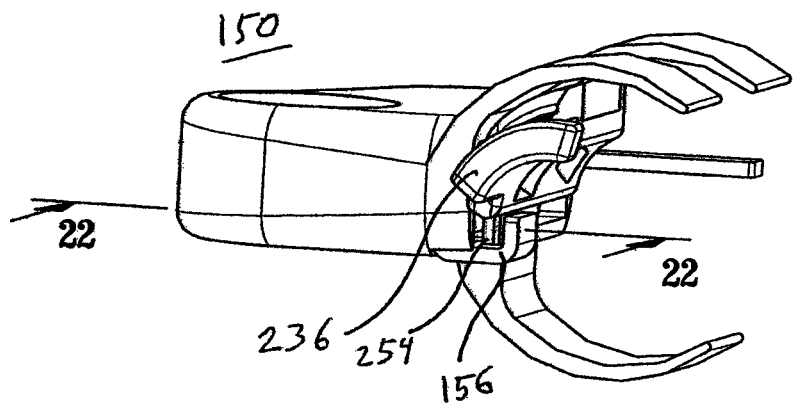
FIG. 21 is a perspective view of the locking shipping wedge incorporating the locking mechanism and in the locked position.
Figure 22:
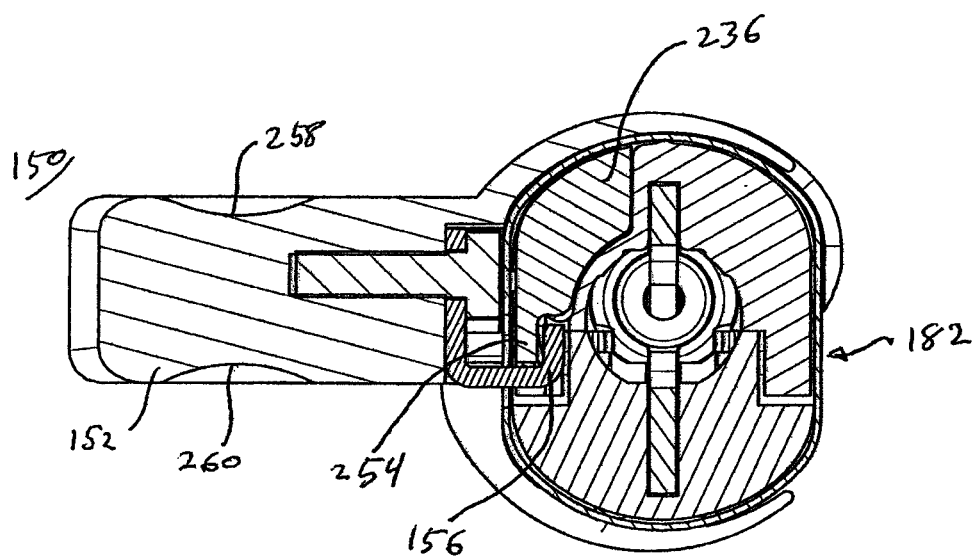
FIG. 22 is a cross sectional view taken along line 22-22 of FIG. 21.
Figure 25:
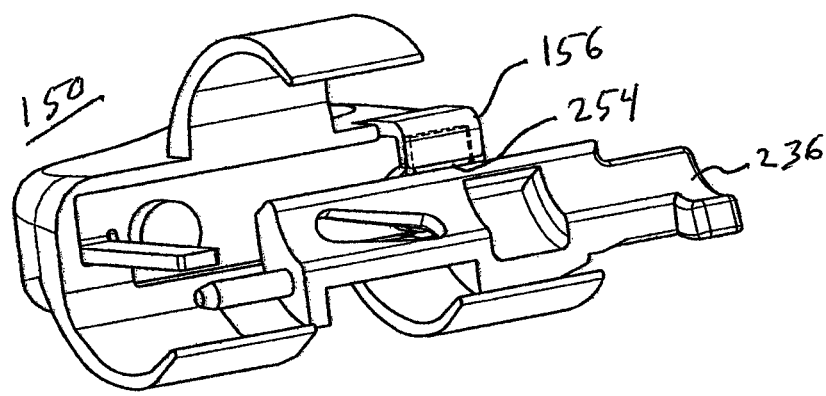
FIG. 25 is a perspective view of the locking shipping wedge and a locking member actuator of the proximal body portion in a locked position.

Referring now to FIGS. 21, 22 and 25, in the initial position, locking lip 156 of shipping wedge 150 is fully engaged with tab 254 formed on locking member actuator 236 to prevent removal of locking shipping wedge 150 from proximal body portion 182. Referring to FIG. 22, locking shipping wedge 150 and, specifically body portion 152, may be provided with a pair of thumb depressions 258 and 260 to facilitate grasping of locking shipping wedge 150.

Figure 23:
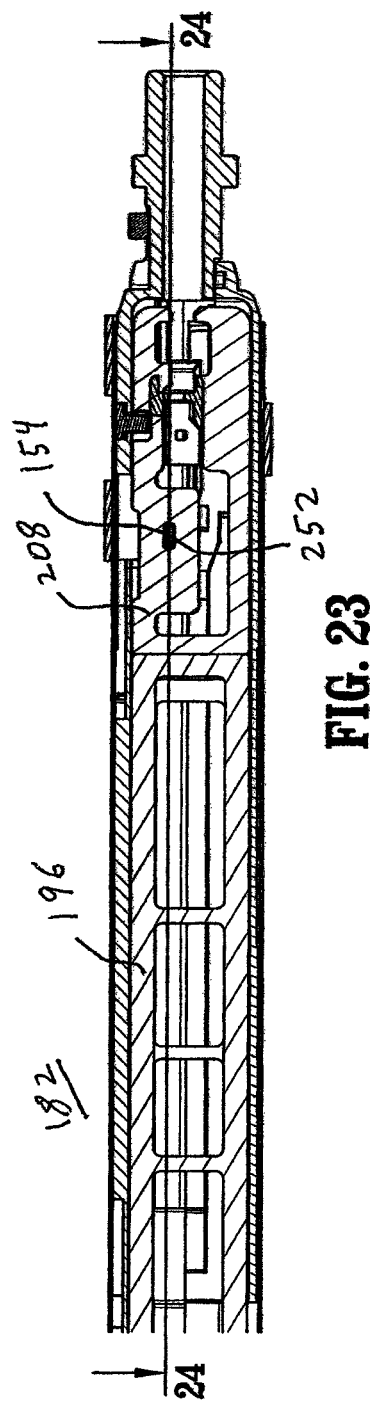
FIG. 23 is a cross-sectional view taken along line 23-23 of FIG. 19.
Figure 24:
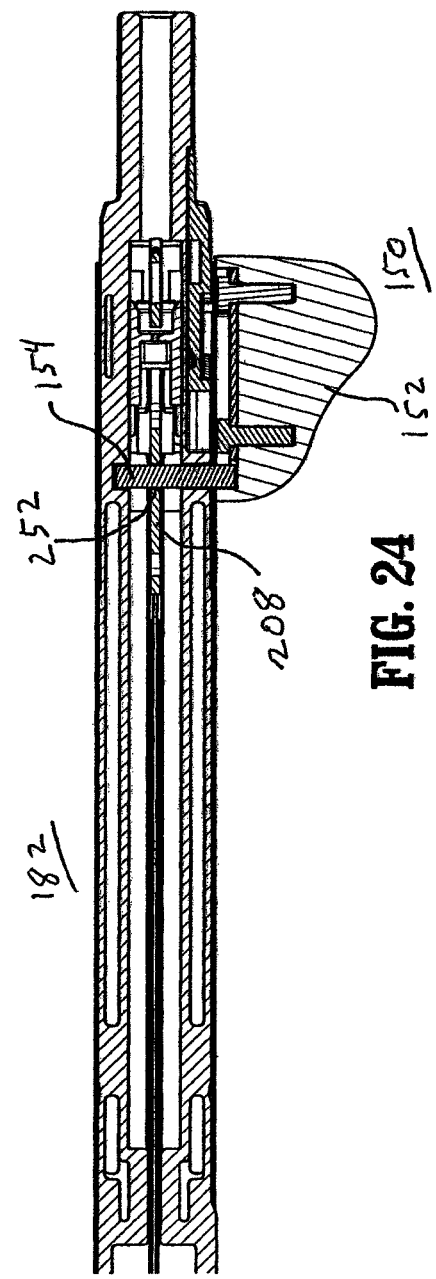
FIG. 24 is a cross-sectional view taken along line 24-24 of FIG. 23.

As best shown in FIGS. 23 and 24, transverse member 154 of locking shipping wedge 150 is fully inserted within slot 252 formed through proximal engagement section 208 of drive assembly 196. This prevents any movement of drive assembly 196 and within proximal body portion 182 of loading unit 150 (FIG. 20).

Figure 26:
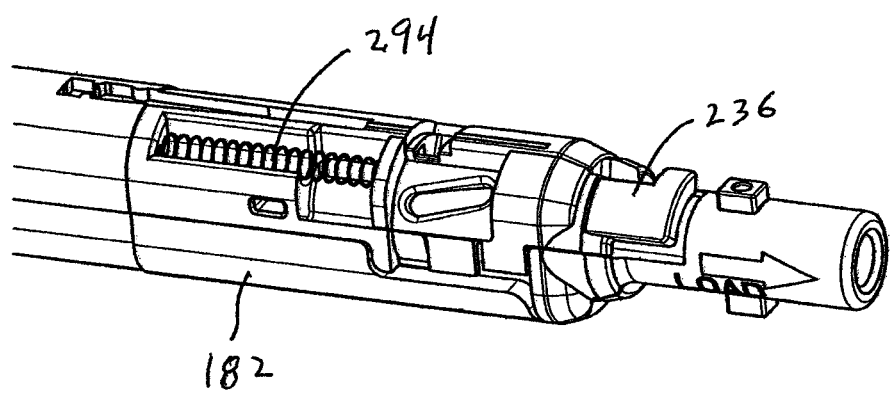
FIG. 26 is a perspective view of the proximal end of the proximal body portion prior to insertion into a surgical stapling instrument.
Figure 28:
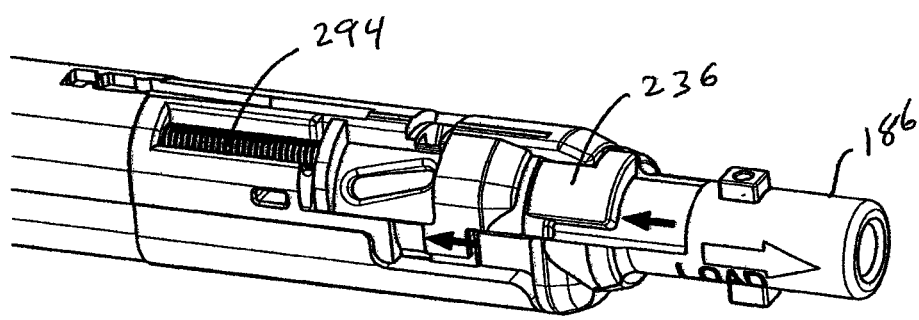
FIG. 28 is a perspective view of the proximal end of the proximal body portion during movement of the locking member actuator to the unlocked position.

Referring now to FIG. 26, in the initial position, locking member actuator 236 is in a proximal most position within proximal body portion 182 due to the bias of spring 294. Upon assembly of loading unit 180 to a surgical stapling instrument, insertion tip 186 is inserted into an elongate member associated with the surgical stapling instrument to cause locking member actuator 236 to be driven distally against the bias of spring 294 (FIG. 28).

Figure 27:
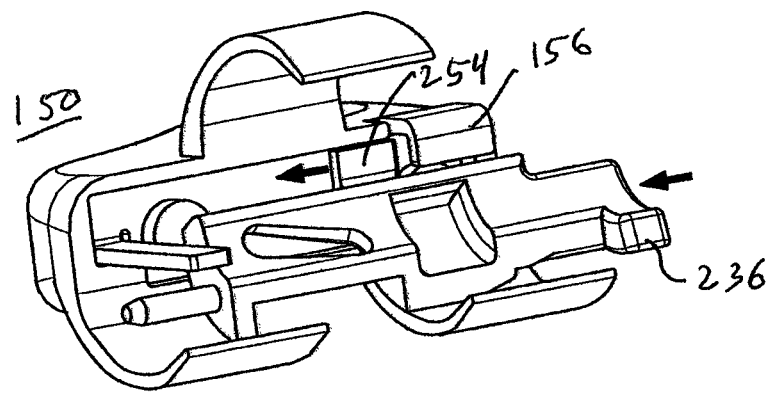
FIG. 27 is a perspective view similar to FIG. 25 illustrating the locking shipping wedge and locking member actuator with the locking member actuator being moved to the unlocked position.
Figure 29:
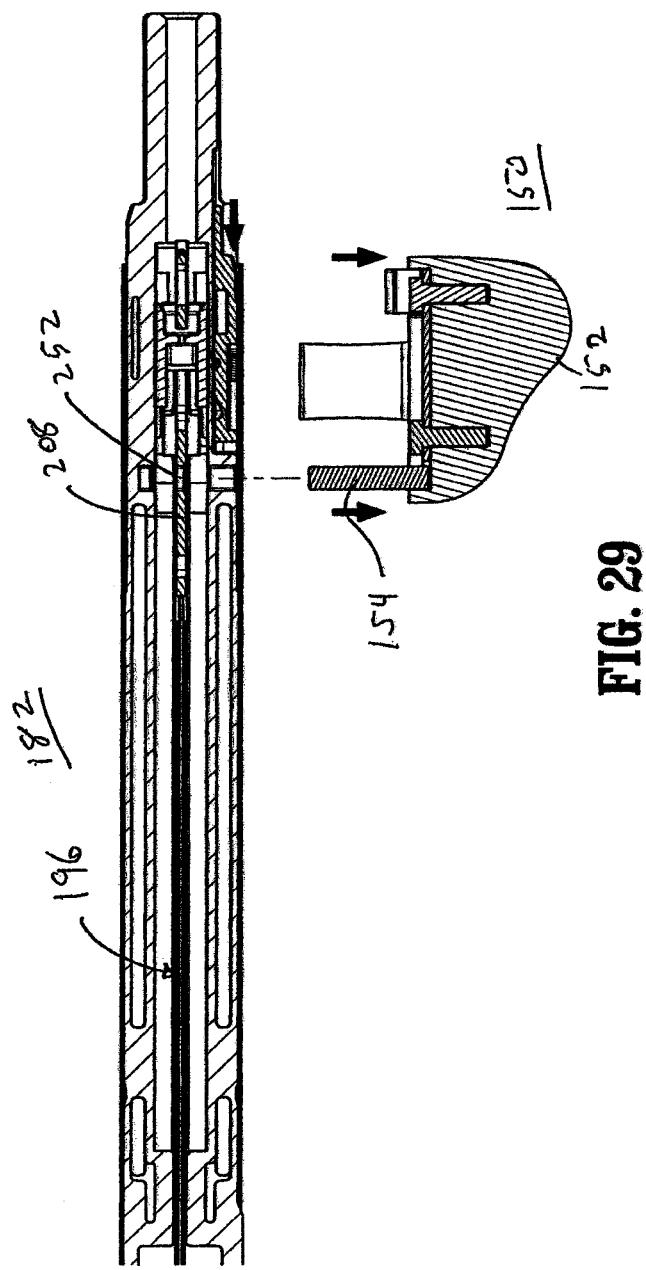
FIG. 29 is a cross sectional view of the proximal body portion and locking shipping wedge during removal of the locking shipping wedge from the single use loading unit.
Figure 30:
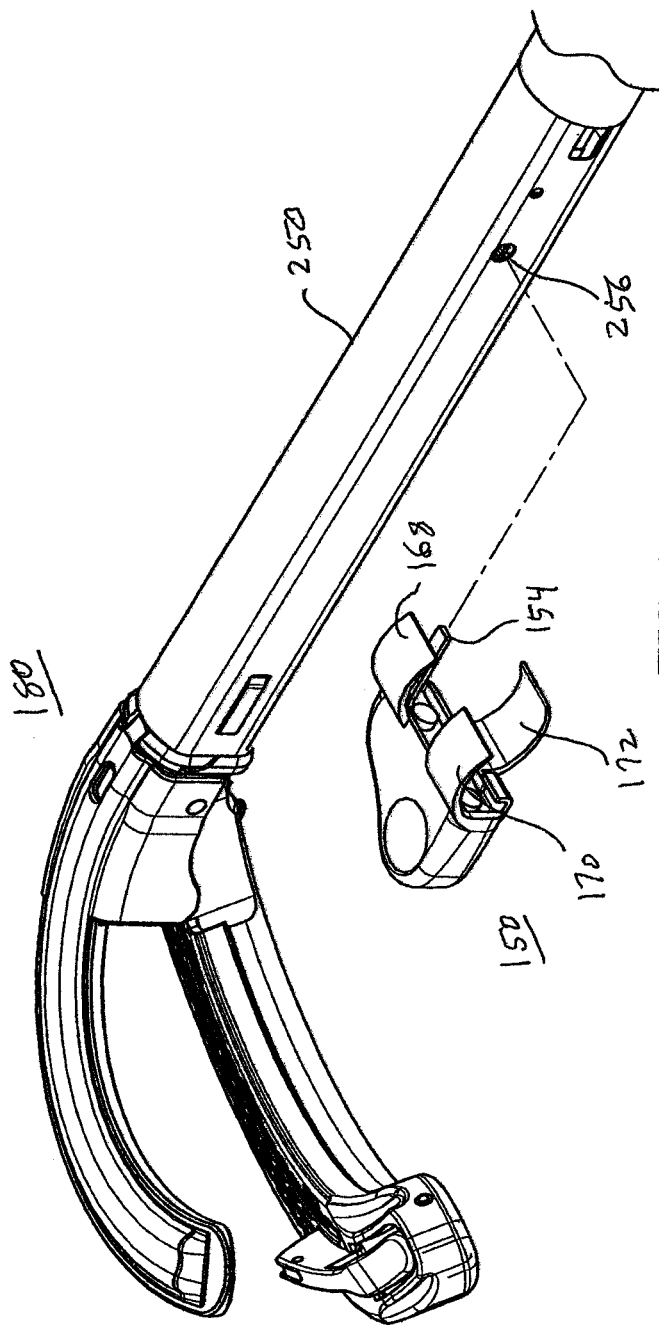
FIG. 30 is a perspective view illustrating removal of the locking shipping wedge from the single use loading unit.

As best shown in FIG. 27, as locking member actuator 236 is driven distally, tab 254 is driven out of engagement with lip 156 on locking shipping wedge 150. Thereafter, with reference to FIG. 29, shipping wedge 150 may be drawn away from proximal body portion 182 to withdraw transverse member 154 out of slot 252 in proximal engagement section 208 of drive assembly 196 thereby releasing drive assembly 196 from shipping wedge 150. As shown in FIG. 30, to disengage shipping wedge 150 from loading unit 180 transverse member 154 is withdrawn through hole 256 formed in outer sleeve 250 and clips 168, 170 and 172 are disengaged from outer sleeve 250.

It will be understood that various modifications may be made to the embodiments disclosed herein. For example, the disclosed transverse members may have other configurations such as, for example, rectangular, triangular, etc. Further, as noted hereinabove, the various components of the disclosed locking shipping wedge as may be formed interleague or may be formed separately and joined by known means such as, for example, welding, gluing, etc. It is also contemplated that the locking shipping wedge disclosed herein can be adapted for use with other locking mechanisms such as those disclosed in U.S. Pat. Nos. 7,097,089, 7,143,924 and U.S. Publication No. 2005/0184123, each of which is incorporated herein, in its entirety, by reference. Therefore, the above description should not be construed as limiting, but merely as exemplifications of particular embodiments. Those skilled in the art will envision other modifications within the scope and spirit of the claims appended hereto.

What is claimed is:

1. A loading unit comprising:
    a body portion adapted to be releasably secured to a surgical instrument;
    a tool assembly coupled to the body portion;
    a drive assembly movable from a retracted position to an advanced position to actuate the tool assembly;
    a shipping wedge removably supported on the body portion to prevent movement of the drive assembly to the advanced position; and
    a locking assembly moveable from a first position in engagement with the shipping wedge preventing removal of the shipping wedge from the body portion to a second position facilitating removal of the shipping wedge from the body portion, wherein movement of the locking assembly from the first position to the second position occurs in response to securement of the body portion to the surgical instrument.

2. The loading unit according to claim 1, wherein the locking assembly includes a locking member and a locking member actuator.

3. The loading unit according to claim 2, wherein the locking member actuator includes a tab and the shipping wedge includes a locking lip, wherein the tab is aligned with the locking lip when the locking assembly is in the first position to prevent removal of the shipping wedge from the body portion and the tab is misaligned with the locking lip when the locking assembly is moved to the second position to facilitate removal of the shipping wedge from the body portion.

4. The loading unit according to claim 2, wherein the locking mechanism includes a lock plate slidably supported within the body portion, the lock plate defining a keyhole including a locking portion and a release portion, wherein the keyhole is dimensioned to receive a locking member of the shipping wedge.

5. The loading unit according to claim 4, wherein the lock plate is movable from a first position in which the locking portion of the keyhole is aligned with the locking member of the shipping wedge to prevent the removal of a shipping wedge from the body portion to a second position in which the release portion of the keyhole is aligned with the locking member of the shipping wedge to facilitate removal of the shipping wedge from the body portion in response to movement of the locking assembly from the first position to the second position.

6. The loading unit according to claim 4, wherein the lock plate includes a finger and the locking actuator member defines a notch for engaging the finger.

7. The loading unit according to claim 1, wherein the tool assembly includes an anvil assembly and a cartridge assembly.

* * * * *